(12) United States Patent
Otsuki et al.

(10) Patent No.: US 7,663,752 B2
(45) Date of Patent: Feb. 16, 2010

(54) POLARIZATION MODULATION IMAGING ELLIPSOMETER

(75) Inventors: Soichi Otsuki, Takamatsu (JP); Mitsuru Ishikawa, Takamatsu (JP)

(73) Assignee: National Institute of Advanced Industrial Science and Technology, Tokyo-To (JP)

( * ) Notice: Subject to any disclaimer, the term of this patent is extended or adjusted under 35 U.S.C. 154(b) by 415 days.

(21) Appl. No.: 11/785,134

(22) Filed: Apr. 16, 2007

(65) Prior Publication Data

US 2008/0049224 A1    Feb. 28, 2008

(30) Foreign Application Priority Data

Aug. 25, 2006   (JP)   ............... 2006-229493

(51) Int. Cl.
    *G01J 4/00* (2006.01)
(52) U.S. Cl. ...................... 356/364; 250/225
(58) Field of Classification Search ......... 356/364–370; 250/250, 225
    See application file for complete search history.

(56) References Cited

U.S. PATENT DOCUMENTS

| | | | |
|---|---|---|---|
| 5,076,696 A | | 12/1991 | Cohn et al. ................... 31/91 |
| 5,657,126 A | * | 8/1997 | Ducharme et al. ........... 356/369 |
| 5,956,145 A | * | 9/1999 | Green et al. ................ 356/364 |
| 5,956,147 A | * | 9/1999 | Jellison et al. .............. 356/369 |
| 6,483,584 B1 | * | 11/2002 | Lee et al. ..................... 356/369 |
| 6,590,667 B1 | * | 7/2003 | Lee et al. ..................... 356/507 |

OTHER PUBLICATIONS

D. Beaglehole, "Performance of a microscopic imaging ellipsometer", Rev. Sci. Instrum., 59, 2557(1988).
S. N. Jasperson, et al., "An Improved Method for High Reflectivity Ellipsometry Based on a New Polarization Modulation Technique", Rev. Sci. Instrum., 40, 761(1969).
B. Drevillon, et al., "Fast polarization modulated ellipsometer using a microprocessor system for digital Fourier analysis", Rev. Sci. Instrum., 53, 969(1982).

(Continued)

*Primary Examiner*—L. G Lauchman
(74) *Attorney, Agent, or Firm*—Kratz, Quintos & Hanson, LLP

(57) ABSTRACT

A polarization modulation imaging ellipsometer capable of measuring ellipsometric parameters of the surface of a sample for each of the measured points with high precision and at high speed, which has a light source unit that emits light whose intensity periodically changes at a predetermined frequency; an incident-light optical unit having a collimator, a polarizer, and a photoelastic phase modulator which modulates light emitted from the light source unit an emitted-light optical unit having an analyzer which analyzes a polarization state of light that has been reflected from or transmitted through the sample and a two-dimensional detector which converts light received from the analyzer to an electrical signal and outputs the electrical signal; and a control/analysis unit which operates the light source unit and the photoelastic phase modulator at the same frequency, and calculates ellipsometric parameters of each of the measured points.

19 Claims, 3 Drawing Sheets

OTHER PUBLICATIONS

P. Gleyzes, et al., "Profilometrie Picometrique. II. L'Approche Multi-Detecteur et la Detection Synghrone Multiplexee", J. Optics, 26, 251(1995).

A. Dubois, et al., "Real-time reflectivity and topography imagery of depth-resolved microscopic surfaces", Opt. Lett., 24, 309(1999).

M. Akiba, et al., "Full-field optical coherence topography by two-dimensional heterodyne detection with a pair of CCD cameras", Opt. Lett., 28, 816(2003).

Shigeru Ando, et al., "Correlation Image Sensor: Two-Dimensional Matched Detection of Amplitude—Modulated Light", IEEE Trans. Electron Devices, 50, 2059 (2003).

Toru Kurihara, et al., "Real-Time Imaging Ellipsometer Using Three-Phase Correlation Image Sensor", Proc. 20th Sensor Symp., pp. 241-244, Tokyo, 2003.

0. Acher, et al., "Improvements of phase-modulated ellipsometry", Rev. Sci. Instrum., 60, 65(1989).

Gerald E. Jellison, et al., "Two-channel polarization modulation ellipsometer", Appl. Opt., 29, 959(1990).

Takaaki Shimizu, et al., "Ellip some trie Imager Using Correlation Image Sensor and Rotating Polarizer", Proc. Japan Society of Applied Physics, Spring Meeting 2003, 29 p-YS-6, 2003.

* cited by examiner

Time lag 0 cycle

1/4 cycle

1/2 cycle

3/4 cycle

→ Control   ----▶ Signal

POLARIZATION MODULATION IMAGING ELLIPSOMETER

BACKGROUND OF THE INVENTION (1) Field of the Invention

The present invention relates to an imaging ellipsometer based on a polarization modulation method.

(2) Description of the Related Art

Various techniques for determining the physical properties and film thickness of thin films, such as thin films composed of inorganic compounds, metals, and like inorganic materials; thin films composed of biological substances, organic compounds, and like organic substances; etc., have been developed and utilized in various technical fields.

Ellipsometry is a technique that makes it possible to determine the optical properties (e.g., refractive index) and film thickness of thin films by using a light beam to irradiate a thin film formed on a flat substrate. In addition to being able to measure in a vacuum or in air, ellipsometry enables measurement to be conducted in a variety of media, such as water, an organic solvent, and the like by the use of a dedicated container. Moreover, ellipsometry can be used for measuring under various conditions. For example, ellipsometry allows measurements over a wide range of light spectra, from ultraviolet/visible light to infrared light, using, as a light source, various lamps, such as a laser beam light, a halogen lamp light, and a xenon lamp light in addition to a laser beam light. Therefore, ellipsometry can be used to measure both inorganic and organic substances, and is thus employed in various industrial and technical fields.

Ellipsometers are classified into reflection and transmission types depending on the disposition of the sample to be measured. The former type analyzes light that has been reflected from the sample from the measurement beams directed at the sample, and the latter type analyzes transmitted light. Hereinafter, reflection ellipsometers will be explained in detail, but it is a matter of course that the description also applies to transmission ellipsometers.

In measurements using ellipsometry, the polarization state of the incident light is generally divided into a p component (which vibrates in parallel with the plane of incidence), and an s component (which vibrates perpendicular to the plane of incidence). The polarization of incident light changes before and after it is reflected from the surface of a film sample, depending on the properties of the film sample. The change in polarization is expressed by the two ellipsometric parameters of $\Psi$ shown in formula (1) and $\Delta$ shown in formula (2):

$$\Psi = \tan^{-1}(|r_p|/|r_s|) \quad (1)$$

$$\Delta = \delta_{rp} - \delta_{rs} \quad (2)$$

In these formulae, $|r_p|$ represents the absolute value of the reflectance of a p component; $|r_s|$ represents the absolute value of the reflectance of an s component; $\delta_{rp}$ represents a change in the phase of a p component; and $\delta_{rs}$ represents a change in the phase of an s component. To be specific, $\Psi$ represents a change in light intensity occurring when incident light reflects from the surface of a sample, and, similarly, $\Delta$ represents a change in phase. The film thickness and refractive index of a sample can be determined from the parameters obtained by these measurements using a calibration curve obtained by fitting, theoretical transformation, experimentation, or simulation.

The overall arrangement of an ellipsometer is classified into a PCSA, PSCA, or other types. In a PCSA ellipsometer, a first polarizer P and a compensator C (¼ wave plate) are disposed along the incidence path of an incident-light optical unit, and a second polarizer A (hereinafter referred to as an analyzer), and a photomultiplier tube, a photodiode, or other means for detecting emitted light are arranged along the emission path of an emitted-light optical unit. The first polarizer P transmits only the polarization component that has a fixed angle (hereinafter referred to as an azimuth) relative to a predetermined axis of coordinates, and converts randomly polarized light into specific, linearly polarized light; the compensator C converts the linearly polarized light into elliptically polarized light by delaying the phase of one polarized light by 90° relative to another polarized light whose azimuth is perpendicular to the phase of said one polarized light; and the second polarizer A transmits only the polarization component that has a specific azimuth among the light that has been reflected from a sample S. In a PSCA ellipsometer, the compensator C, the analyzer A, and the detector are arranged along the emission path of an emitted-light optical unit.

As shown in the above examples, an ordinary ellipsometer has an incident-light optical unit that irradiates a sample with a luminous flux having a predetermined cross section, and an emitted-light optical unit having a means for detecting an emitted light, such as a photomultiplier tube, photodiode, or the like. Therefore, the optical properties and film thickness of a sample measured using such an ellipsometer are the average optical properties and average film thickness of the sample for the area upon which the luminous flux was irradiated.

However, the film sample to be measured generally has a fixed surface area, and the optical properties and film thickness generally differ from place to place along the surface of the sample. Thus, depending on the measurement purpose, it may be more important to obtain the accurate optical properties and film thickness of the sample for each of the measured points and their distributions, rather than the average optical properties and film thickness of the entire sample. For example, in manufacturing semiconductor processes, since a fine thin-film pattern is formed onto a silicon wafer using photolithography, it is important to determine the composition and thickness of each of several points of the pattern at each step. Recently, in order to manufacture various electronic devices, optical devices, etc., the formation of two-dimensional crystals composed of an organic compound on a solid surface, such as a metal, semiconductor, or derivative, has been studied. This makes it important to determine the optical properties and thickness in two dimensions. Moreover, in order to quickly identify the genes and proteins involved in bio-phenomena, such as for preventing the development of cancer, widespread attention is presently being focused on a technique for efficiently detecting the DNA and proteins contained in samples using a microarray in which various kinds of DNA and antibodies are arranged on a flat substrate. The DNA and proteins contained in a sample are adsorbed on the substrate by specific interactions with the DNA and proteins, respectively, that are fixed on the substrate. A technique for determining, in two dimensions, the DNA and proteins that adsorb on the substrate is indispensable.

There are several reports on two-dimensional measurement using an ellipsometer. For example, according to an imaging ellipsometer with a rotary analyzer disclosed in Patent Document 1, the azimuths of the polarizer and compensator are adjusted to a given angle, the analyzer is rotated, and the reflected light is measured with a CCD camera at the four azimuths of 0°, 45°, −45°, and 90°, after which ρ and Δ are arithmetically calculated from the azimuths of the polarizer, analyzer, and compensator.

According to an imaging ellipsometer disclosed in Non-Patent Document 1, the phase difference δ of a p component relative to an s component of an incident light is changed at given intervals by adjusting the azimuths of a polarizer and compensator to a given angle and rotating a compensator, and the intensity of reflected light is measured with a CCD camera at each phase difference δ, after which Ψ and Δ (hereinafter referred to as ellipsometric parameters) are arithmetically calculated from the obtained intensity values of the reflected light.

However, in these devices, the measurement precision is inferior to ordinary measurements using a single detector, often by an order of magnitude or more, and the measurement takes a long time.

In particular, as compared with the polarization modulation ellipsometer, which allows highly precise measurement, the difference in precision can exceed three or more orders of magnitude. In a polarization modulation ellipsometer, ellipsometric parameters are determined by periodically changing the polarization state of the light used for measuring at frequencies in the range of several tens of kHz to several hundreds of kHz, and performing frequency analysis of the changes in light intensity over time that are measured by a detector. The polarization modulation ellipsometer also features a high S/N ratio in the obtained results. This is because only a specific frequency component of a light signal can be selectively detected, and optical elements are not mechanically driven. In addition, the time required for obtaining ellipsometric parameters is as short as several milliseconds and noise can be easily decreased by extending the measuring time. In the initially announced device, a specific frequency component was detected using a lock-in amplifier (Non-Patent Document 2). A method for performing Fourier transformation of a signal that was subjected to high-speed A/D (analog-to-digital) conversion was then proposed (Non-Patent Document 3). With these devices, ellipsometric parameters Ψ and Δ can generally be measured at a precision of $10^{-3}$ degree and $10^{-2}$ degree, respectively, and when the measuring time is set to about 10 seconds, the precision can be further improved by about $10^{-2}$.

In contrast, since the CCD detection rate reaches video rates (about several tens of Hz to several hundreds of Hz) at most, a CCD cannot detect light signals modulated at several tens of kHz to several hundreds of kHz when the detection rate is maintained in its original condition. Thus, a method for achieving lock-in detection similar to that when using a single detector was developed by periodically changing the intensity of the measuring beam that is directed at the sample at the same fundamental frequency as a phase modulator (Non-Patent Document 4). For example, when a measuring beam is periodically blocked to be converted into a continuously pulsed light, the light signal is detected only while the measuring beam is incident on the sample. This makes it possible to perform frequency analysis of phenomena with high change rates by using minute sensors, each corresponding to a pixel, in a CCD imaging sensor. By basing the ON/OFF duration on the cycle of the drive signal of a phase modulator, the direct-current component of an output signal, a component having the same phase as that of the drive signal of the phase modulator (a sine wave component), and a component having a phase difference of 90° (a cosine wave component) can be extracted. In addition, specific harmonic components can be extracted by modulating the amplitude of the measuring beam using a signal that includes a sine wave and a finite number of harmonic components, thus utilizing the nature of a trigonometric function.

The parallel synchronous detection that is attained by modulating the amplitude of the measuring beam has been applied to light interference microscopes and the like to thereby improve their precision and increase their functions (Non-Patent Documents 5 and 6).

A method for measuring the ellipticity and polarization direction of light in real time was devised by developing a time-correlated image sensor in which the CCD gate is controlled by an external signal (Non-Patent Documents 7, 8 and 9).

[Patent Document 1] U.S. Pat. No. 5,076,696

[Non-Patent Document 1] Rev. Sci. Instrum., 59, 2557(1988)

[Non-Patent Document 2] Rev. Sci. Instrum., 40, 761(1969)

[Non-Patent Document 3] Rev. Sci. Instrum., 53, 969(1982)

[Non-Patent Document 4] J. Optics, 26, 251(1995)

[Non-Patent Document 5] Opt. Lett., 24, 309(1999)

[Non-Patent Document 6] Opt. Lett., 28, 816(2003)

[Non-Patent Document 7] IEEE Trans. Electron Devices, 50, 2059 (2003)

[Non-Patent Document 8] Proc. Japan Society of Applied Physics, Spring Meeting 2003, 29 p-YS-6, 2003

[Non-Patent Document 9] Proc. 20th Sensor Symp., pp. 241-244, Tokyo, 2003

[Non-Patent Document 10] Rev. Sci. Instrum., 60, 65(1989)

[Non-Patent document 11] Appl. Opt., 29, 959(1990)

BRIEF SUMMARY OF THE INVENTION

Problem to be Solved by the Invention

However, the application of parallel synchronous detection, achieved by modulating the amplitude of a measuring beam, to imaging ellipsometers has not been achieved. With a light interference microscope and the like, the target measurement can be satisfactorily performed as long as the relative value of the measurement signal can be reproduced. However, an ellipsometer requires strict calibration of the device characteristics in the measurement signal in order to determine accurate ellipsometric parameters. In an ellipsometer using a single detector, a method for calibrating the device characteristics by measuring a standard sample and determining a signal component depending on the device characteristics from a specific frequency component obtained using a lock-in amplifier or the like is known (Non-Patent Documents 2 and 3). However, a method for obtaining an accurate ellipsometric parameter by calibrating the device characteristics and simultaneously performing measurement with parallel synchronous detection using a CCD as a detector has not been reported.

Due to the operating principle of the methods disclosed in the above-mentioned Non-Patent Documents 7 to 9, there is a limit to the number of imaging elements that can be increased because the elements are in the research stage and the circuit structure is complicated.

In order to solve the above-described problems, the invention aims to provide a polarization modulation imaging ellipsometer capable of determining ellipsometric parameters Ψ and Δ in each pixel of an image corresponding to each of several points of the surface of a sample with high precision and at high speed by performing measurement while modulating a measurement beam with a photoelastic phase modulator at a frequency in the range of several tens of kHz to several hundreds of kHz and using calibration values of device characteristics obtained in advance.

The object of the present invention is achieved by the following methods.

A polarization modulation imaging ellipsometer (1) of the invention having a light source unit that emits light whose amplitude periodically changes at a predetermined frequency;

a sample holder on which a sample is placed;

an incident-light optical unit having a collimator, a polarizer, and a photoelastic phase modulator which modulates light emitted from the light source unit to sinusoidally vary a phase difference between a p polarized light and an s polarized light of the light and applies the light to a measurement plane of the sample placed on the sample holder;

an emitted-light optical unit having an analyzer which analyzes a polarization state of light that has been reflected from or transmitted through the sample and a two-dimensional detector which converts light received from the analyzer to an electrical signal and outputs the electrical signal;

a control/analysis unit which operates the light source unit and the photoelastic phase modulator at the same frequency in a range of several tens of kHz to several hundreds of kHz, and to which an output signal emitted from the two-dimensional detector is input; wherein the polarizer, the photoelastic phase modulator, the sample, and the analyzer are arranged in this order on a light path, resulting in a PMSA type (polarizer-modulator-sample-analyzer) arrangement;

the light source unit sequentially produces a measuring beam having a predetermined time lag relative to an operation clock of the photoelastic phase modulator; and the control/analysis unit calculates ellipsometric parameters $\Psi$ and $\Delta$ for each pixel of a two-dimensional image of a surface of the sample to be observed with the two-dimensional detector using an output signal of the two-dimensional detector under conditions (1) to (3):

(1) amplitude intensity of light that has passed through the photoelastic phase modulator being expressed as "$\alpha$", an mth order Bessel function of the first kind being expressed as $J_m(\alpha)$ in which m is an integer equal to or greater than 0 and the amplitude intensity $\alpha$ is a variable, a factor containing $J_m(\alpha)$ in which m is an odd number being expressed as $J_S$, and a factor containing $J_m(\alpha)$ in which m is an even number being expressed as $J_C$;

(2) a direct-current component of light intensity detected by the detector being expressed as $I_{DC}$, amplitude intensity of a sine wave component of light intensity detected by the detector being expressed as $I_S$, and amplitude intensity of a cosine wave component of light intensity detected by the detector being expressed as $I_C$, azimuths of the polarizer, photoelastic phase modulator, and analyzer being expressed as P, M, and A, respectively, and $I_{DC}$, $I_S$, and $I_C$ being represented by $I_{DC} =$ $(1 - \cos 2\Psi \cos 2A) + \cos 2(P - M) \cos 2M (\cos 2A - \cos 2\Psi) +$ $\sin 2A \cos \Delta \cos 2(P - M) \sin 2\Psi \sin 2M$ -continued $I_S = \sin 2(P - M) \sin 2A \sin 2\Psi \sin \Delta$ $I_C = \sin 2(P - M)[(\cos 2\Psi - \cos 2A) \sin 2M + \sin 2A \cos 2M \sin 2\Psi \cos \Delta];$ (3) a sine wave component of the output signal of the two-dimensional detector being expressed as $S_S$, a cosine wave component of the output signal of the two-dimensional detector being expressed as $S_C$, a direct-current component of the output signal of the two-dimensional detector being expressed as $S_{DC}$, and $R_S = S_S/S_{DC}$ and $R_C = S_C/S_{DC}$; wherein when the photoelastic phase modulator is ideal, the ellipsometric parameters $\Psi$ and $\Delta$ are calculated based on equation 1:

$$R_S = \frac{I_S J_S}{I_{DC} + I_C J_0(\alpha)} \quad \text{[Equation 1]}$$

and $$R_C = \frac{I_C J_C}{I_{DC} + I_C J_0(\alpha)}$$

and when the photoelastic phase modulator has static phase difference $\delta_0$, the ellipsometric parameters $\Psi$ and $\Delta$ are calculated based on equation 2:

$$R_S = \frac{(I_S - I_C \sin \delta_0) J_S}{I_{DC} + (I_C + I_S \sin \delta_0) J_0(\alpha)} \quad \text{[Equation 2]}$$

and $$R_C = \frac{(I_C + I_S \sin \delta_0) J_C}{I_{DC} + (I_C + I_S \sin \delta_0) J_0(\alpha)}.$$

A polarization modulation imaging ellipsometer (2) of the invention having a light source unit that emits light whose amplitude periodically changes at a predetermined frequency;

a sample holder on which a sample is placed;

an incident-light optical unit having a collimator and a polarizer;

an emitted-light optical unit having a photoelastic phase modulator which modulates light that has been reflected from or transmitted through the sample to sinusoidally vary a phase difference between a p polarized light and an s polarized light of the light, an analyzer which analyzes the polarization state of light that has been transmitted through the photoelastic phase modulator, and a two-dimensional detector which converts light received from the analyzer into an electrical signal and outputs the electrical signal;

a control/analysis unit which operates the light source unit and the photoelastic phase modulator at the same frequency in a range of several tens of kHz to several hundreds of kHz, and to which an output signal emitted from the two-dimensional detector is input; wherein the polarizer, the sample, the photoelastic phase modulator, and the analyzer are arranged in this order on a light path, resulting in a PSMA type (polarizer-sample-modulator-analyzer) arrangement;

the light source unit sequentially produces a measuring beam having a predetermined time lag relative to an operation clock of the photoelastic phase modulator; and the control/analysis unit calculates ellipsometric parameters $\Psi$ and $\Delta$ for each pixel of a two-dimensional image of a surface of the sample to be observed with the two-dimensional detector using an output signal of the two-dimensional detector under conditions (1) to (3):

(1) amplitude intensity of light that has passed through the photoelastic phase modulator being expressed as "$\alpha$", an mth order Bessel function of the first kind being expressed as $J_m(\alpha)$ in which m is an integer equal to or greater than 0 and the amplitude intensity $\alpha$ is a variable, a factor containing $J_m(\alpha)$ in which m is an odd number being expressed as $J_S$, and a factor containing, $J_m(\alpha)$ in which m is an even number being expressed as $J_C$;

(2) a direct-current component of light intensity detected by the detector being expressed as $I_{DC}$, amplitude intensity of a sine wave component of light intensity detected by the detector being expressed as $I_S$, and amplitude intensity of a cosine wave component of light intensity detected by the detector being expressed as $I_C$, azimuths of the polarizer, photoelastic phase modulator, and analyzer being expressed as P, M, and A, respectively, and $I_{DC}$, $I_S$, and $I_C$ being represented by 
$$I_{DC} = (1 - \cos 2\Psi \cos 2P) + \cos 2(A - M) \cos 2M (\cos 2P - \cos 2\Psi) + \sin 2P \cos \Delta \cos 2(A - M) \sin 2\Psi \sin 2M$$
$$I_S = \sin 2(A - M) \sin 2P \sin 2\Psi \sin \Delta$$
$$I_C = \sin 2(A - M)[(\cos 2\Psi - \cos 2P)\sin 2M + \sin 2P \cos 2M \sin 2\Psi \cos \Delta];$$

(3) a sine wave component of the output signal of the two-dimensional detector being expressed as $S_S$, a cosine wave component of the output signal of the two-dimensional detector being expressed as $S_C$, a direct-current component of the output signal of the two-dimensional detector being expressed as $S_{DC}$, and $R_S = S_S/S_{DC}$ and $R_C = S_C/S_{DC}$; wherein when the photoelastic phase modulator is ideal, the ellipsometric parameters $\Psi$ and $\Delta$ are calculated based on equation 3:

$$R_S = \frac{I_S J_S}{I_{DC} + I_C J_0(\alpha)} \quad [\text{Equation 3}]$$

and $$R_C = \frac{I_C J_C}{I_{DC} + I_C J_0(\alpha)}$$

and when the photoelastic phase modulator has static phase difference $\delta_0$, the ellipsometric parameters $\Psi$ and $\Delta$ are calculated based on equation 4:

$$R_S = \frac{(I_S - I_C \sin \delta_0) J_S}{I_{DC} + (I_C + I_S \sin \delta_0) J_0(\alpha)} \quad [\text{Equation 4}]$$

and $$R_C = \frac{(I_C + I_S \sin \delta_0) J_C}{I_{DC} + (I_C + I_S \sin \delta_0) J_0(\alpha)}$$

According to a polarization modulation imaging ellipsometer (3) of the invention, in the polarization modulation imaging ellipsometer (1) or (2), the light source unit sequentially produces four kinds of measuring beams, each measuring beam having a rectangular wave in which an ON duration is ¼ cycle and a time lag is 0, ¼, ½, or ¾ cycle relative to an operation clock of the photoelastic phase modulator; and the control/analysis unit acquires output signals of the two-dimensional detector that are obtained by sequential production of the four kinds of measuring beams each having a time lag of 0, ¼, ½, or ¾ cycle, and the obtained output signals being denoted as $S_0$, $S_1$, $S_2$, and $S_3$ respectively corresponding to time lags of 0, ¼, ½, and ¾ cycle, and calculates $S_S$, $S_C$, and $S_{DC}$ values by the following equations:

$$S_S = S_3 - S_1,$$

$$S_C = S_0 - S_1 + S_2 - S_3, \text{ and}$$

$$S_{DC} = S_0 + S_1 + S_2 + S_3.$$

According to a polarization modulation imaging ellipsometer (4) of the invention, in the polarization modulation imaging ellipsometer (1) or (2), when the light source unit sequentially produces two kinds of measuring beams, each measuring beam having a rectangular wave in which the ON duration is ½ cycle and a time lag of 0 or ½ cycle relative to an operation clock of the photoelastic phase modulator;

the control/analysis unit acquires output signals of the two-dimensional detector that are obtained by sequential production of the two kinds of measuring beams having time lags of 0 and ½ cycle, and are denoted as $S_0$ and $S_1$, respectively, calculates $S_S$ and $S_{DC}$ values by the following equations:

$$S_S = S_0 - S_1, \text{ and } S_{DC} = S_0 + S_1; \text{ and}$$

when the light source unit sequentially produces a first measuring beam in which the ON duration is ¼ cycle and a second measuring beam whose phase is opposite to that of the first measuring beam and in which the ON duration is ¾ cycle;

the control/analysis unit acquires output signals of the two-dimensional detector that are obtained by sequential production of the first and second measuring beams, and are denoted as $S_2$ and $S_3$, respectively, and calculates $S_C$ and $S_D$ values by the following equations:

$$S_C = (3S_2 - S_3)/2, \text{ and } S_{DC} = S_3 + S_3.$$

According to a polarization modulation imaging ellipsometer (5) of the invention, in the polarization modulation imaging ellipsometer (1) or (2), the light source unit sequentially produces four kinds of measuring beams each having an amplitude $M_p$ expressed by the following function:

$$M_p(t) = 1 + 2 \cos[\omega(t + p/4f - \pi/2)] + 2 \cos[2\omega(t + p/4f)],$$

where f denotes the frequency of an operation clock of the photoelastic phase modulator, $\omega$ denotes an angular frequency, p is an integer from 0 to 3, and t is a time; and the control/analysis unit acquires output signals of the two-dimensional detector obtained by sequential production of the four kinds of measuring beams, and calculates $S_S$, $S_C$, and $S_{DC}$ values by the following equations:

$$S_S = S_1 - S_3,$$

$$S_C = S_0 - S_1 + S_2 - S_3, \text{ and}$$

$$S_{DC} = S_0 + S_1 + S_2 + S_3; \text{ wherein}$$

$S_0$, $S_1$, $S_2$, and $S_3$ are output signals corresponding to p=0, 1, 2, and 3 respectively.

According to a polarization modulation imaging ellipsometer (6) of the invention, in the polarization modulation imaging ellipsometer (1) or (2), the light source unit sequentially produces four kinds of measuring beams each having amplitudes $M_{1p}$ or $M_{2p}$ expressed by functions:

$$M_{1p}(t)=1+2\cos[\omega(t+p/4f)-\pi/2] \text{ and}$$

$$M_{2p}(t)=1+2\cos[2\omega(t+p/4f)]; \text{ wherein}$$

$\omega$ denotes angular frequency of an operation clock of the photoelastic phase modulator, p is 0 or 1, and t is a time;

the control/analysis unit acquires output signals of the two-dimensional detector obtained by sequential production of the four kinds of measuring beams, and calculates $S_S$, $S_C$ and $S_{DC}$ values by the following equations:

$$S_S = S_{10} - S_{11},$$

$$S_C = S_{20} - S_{21}, \text{ and}$$

$$S_{DC} = S_{10} + S_{11} \text{ or } S_{DC} = S_{20} + S_{21}, \text{ wherein}$$

$S_{10}$ and $S_{11}$ are output signals corresponding to $M_{1p}$ with p=0 and 1 respectively, and $S_{20}$ and $S_{21}$ are output signals corresponding to $M_{2p}$ with p=0 and 1 respectively.

According to a polarization modulation imaging ellipsometer (7) of the invention, the polarization modulation imaging ellipsometer (1) or (2), azimuth indicated by graduation of the polarizer, photoelastic phase modulator, and analyzer is denoted as P', M', and A', respectively;

the control/analysis unit calibrates the P, M, and A using the following equations:

$$P = P' - P_0$$

$$M = M' - M_0$$

$$A = A' - A_0, \text{ wherein}$$

$M_0$ and $A_0$ are values of M' and A', respectively, when an average of each $S_S$ and $S_C$ in an aperture of the photoelastic phase modulator becomes equal to 0 in the case where P'=45° and a sample having ellipsometric parameter $\Psi$ in a range of 30°<$\Psi$<60° or in a range of 120°<$\Psi$<150° and ellipsometric parameter $\Delta$ in a range of 70°<$\Delta$<110° is used; and $P_0$ is a value of P' when an average of each $S_S$ and $S_C$ in the aperture of the photoelastic phase modulator becomes equal to 0 in the case where M' is equal to 0°+$M_0$, A' is equal to 45°+$A_0$ and a sample having ellipsometric parameter $\Psi$ in a range of 30°<$\Psi$<60° or in a range of 120°<$\Psi$<150° and an ellipsometric parameter $\Delta$ in a range of 70°<$\Delta$<110° is used.

According to a polarization modulation imaging ellipsometer (8) of the invention, in the polarization modulation imaging ellipsometer (1) or (2), $\alpha$ is 137.8°, which is the value when $J_0(\alpha)$ becomes equal to 0; and $J_S$ and $J_C$ are calculated from the $\alpha$ value.

According to a polarization modulation imaging ellipsometer (9) of the invention, in the polarization modulation imaging ellipsometer (1) or (2), for each wavelength which needs to be measured, when the photoelastic phase modulator has a static phase difference $\delta_0$, the control/analysis unit performs measurement using a standard sample, whose ellipsometric parameters are known, and the circular area which is concentric with a circle whose diameter is an aperture diameter of an area having 99% or more of amplitude intensity in the photoelastic phase modulator and whose diameter is 80% or less of the aperture diameter; and the control/analysis unit calculates an average $\delta_0$ in the aperture diameter of the photoelastic phase modulator using equation 5:

$$R_S^{cal,av} = \frac{(I_S^{cal} - I_C^{cal}\sin\delta_0)J_S}{I_{DC}^{cal}} \quad \text{[Equation 5]}$$

$$R_C^{cal,av} = \frac{(I_C^{cal} + I_S^{cal}\sin\delta_0)J_C}{I_{DC}^{cal}}, \text{ wherein}$$

$I_{DC}$, $I_S$, and $I_C$, which have been calculated by substituting the known ellipsometric parameters $\Psi$ and $\Delta$, are denoted as $I_{DC}^{cal}$, $I_S^{cal}$, and $I_C^{cal}$; and averages of calibration values of the $R_S$ and $R_C$ in the circular area whose diameter is the aperture diameter determined using the standard sample are denoted as $R_S^{cal,av}$ and $R_C^{cal,av}$.

According to a polarization modulation imaging ellipsometer (10) of the invention, in the polarization modulation imaging ellipsometer (1) or (2), the control/analysis unit calculates the ellipsometric parameters $\Psi$ and $\Delta$ using a measurement result obtained by using a circular area which is concentric with a circle whose diameter is an aperture diameter of an area having 99% or more of amplitude intensity in the photoelastic phase modulator and whose diameter is 80% or less of the aperture diameter and by assuming that amplitude intensity is uniform in the circular area.

According to a polarization modulation imaging ellipsometer (11) of the invention, in the polarization modulation imaging ellipsometer (1) or (2), the control/analysis unit performs measurement using at least two kinds of standard samples having different ellipsometric parameters $\Psi$ and $\Delta$, values of $I_{DC}$, $I_S$, and $I_C$ calculated by substituting known ellipsometric parameters $\Psi$ and $\Delta$ of the standard sample being denoted as $I_{DC}^{cal}$, $I_S^{cal}$, and $I_C^{cal}$, respectively, and the values of $R_S$ and $R_C$ measured using the standard sample being denoted as $R_S^{cal}$ and $R_C^{cal}$, respectively;

the control/analysis unit calculates at least two kinds of two formulae represented by the following equations 6 and 7, equation 6 being used when the photoelastic phase modulator is ideal, and equation 7 being used when the photoelastic phase modulator has static phase difference $\delta_0$:

$$R_S^{cal} = \frac{I_S^{cal}J_S}{I_{DC}^{cal} + I_C^{cal}J_0(\alpha)} \quad \text{[Equation 6]}$$

$$R_C^{cal} = \frac{I_C^{cal}J_C}{I_{DC}^{cal} + I_C^{cal}J_0(\alpha)}$$

$$R_S^{cal} = \frac{(I_S^{cal} - I_C^{cal}\sin\delta_0)J_S}{I_{DC}^{cal} + (I_C^{cal} + I_S^{cal}\sin\delta_0)J_0(\alpha)} \quad \text{[Equation 7]}$$

$$R_C^{cal} = \frac{(I_C^{cal} + I_S^{cal}\sin\delta_0)J_C}{I_{DC}^{cal} + (I_C^{cal} + I_S^{cal}\sin\delta_0)J_0(\alpha)}$$

$J_0(\alpha)$ being determined from said at least four formulae; and the control/analysis unit determines amplitude intensity $\alpha$ in each point in an aperture of the photoelastic phase modulator using a look-up table in which a relationship between $\alpha$ and $J_0(\alpha)$ has been calculated in advance.

According to a polarization modulation imaging ellipsometer (12) of the invention, in the polarization modulation imaging ellipsometer (11), when the photoelastic phase modulator is an element plate cut into a regular octagon, the control/analysis unit determines three unknown parameters $x_0$, $y_0$, and $r_0$ by performing fitting the amplitude intensity $\alpha$ measured at each point within the aperture diameter to a formula represented by the following equation:

$$\alpha = \alpha_0 \cos\left\{\frac{\pi}{2} \frac{[(x-x_0)^2 + (y-y_0)^2]^{1/2}}{r_0}\right\}, \text{wherein} \quad \text{[Equation 8]}$$

($X_0$, $y_0$) is a position of a center of the element plate, $\alpha_0$ is a value of $\alpha$ at the center, $r_0$ is a distance between the center and a point where $\alpha=0$, and, using the amplitude intensity $\alpha$ measured at each point within the aperture diameter, or when the photoelastic phase modulator is an element plate cut into a rectangle, the control/analysis unit determines two unknown parameters $y_0$ and $r_0$ by measuring amplitude intensity $\alpha$ at each point within the aperture, averaging values which are obtained at positions each having the same y and different x in a transverse direction, and performing fitting the averaged amplitude intensity $\alpha$ to a formula represented by the following equation:

$$\alpha = \alpha_0 \cos\left(\frac{\pi}{2} \frac{|y-y_0|}{r_0}\right), \text{wherein} \quad \text{[Equation 9]}$$

$y_0$ is a height at the center in the minor axis direction, $\alpha_0$ is a value of $\alpha$ at the center, $r_0$ is a distance between the center and a point where $\alpha=0$, and, using the amplitude intensity $\alpha$ measured at each point within the aperture diameter, and thereby the control/analysis unit determines a calibration value for amplitude intensity $\alpha$ at each point within the aperture.

According to a polarization modulation imaging ellipsometer (13) of the invention, in the polarization modulation imaging ellipsometer (1) or (2), when the light source unit sequentially produces two kinds of measuring beams each having an ON duration of ¼ cycle and having a time lag of ¼ or ¾ cycle relative to an operation clock of the photoelastic phase modulator;

the control/analysis unit acquires output signals of the two-dimensional detector obtained by the sequential production of the two kinds of measuring beams, each measuring beam having a time lag of ¼ or ¾ cycle; calculates the $S_S$ value using the equation $S_S = S_4 - S_5$, wherein $S_4$ and $S_5$ denote the acquired output signals corresponding to time lags of ¼ or ¾ cycle; and denotes the $S_S$ value as $S_{S1}$;

when the light source unit sequentially produces two kinds of measuring beams each having an ON duration of ½ cycle and having a time lag of 0 or ½ cycle relative to an operation clock of the photoelastic phase modulator;

the control/analysis unit acquires output signals of the two-dimensional detector obtained by the sequential production of the two kinds of measuring beams, each measuring beam having a time lag of 0 or ½ cycle; calculates the Ss value using the equation $S_S = S_6 - S_7$, wherein $S_6$ and $S_7$ denote the acquired output signals corresponding to time lags of 0 or ½ cycle; and denotes the $S_S$ value as $S_{S2}$; and the control/analysis unit calculates an actual measurement value of $S_{S1}/S_{S2}$, which is a ratio of two sine wave component values $S_{S1}$ and $S_{S2}$; and determines $J_S$, $J_C$, $J_0(\alpha)$ according to a look-up table obtained by calculation beforehand using a relationship expression represented by equation 10:

$$S_{S1}/S_{S2} = \frac{\sum_{m=0}^{\infty}\left\{(-1)^m \frac{J_{2m+1}(\alpha)}{2m+1}\sin[(2m+1)\pi/4]\right\}}{\sum_{m=0}^{\infty} \frac{J_{2m+1}(\alpha)}{2m+1}}. \quad \text{[Equation 10]}$$

According to a polarization modulation imaging ellipsometer (14) of the invention, in the polarization modulation imaging ellipsometer (1) or (2), the control/analysis unit acquires the output signals of the two-dimensional detector obtained by the sequential production of the measuring beams calculates the $S_S$; and the light source unit further sequentially produces two kinds of measuring beams represented by a formula $M_{3p}(t) = 1+2\cos[3\omega(t+p/6f)-\pi/2]$, wherein $\omega$ denotes an angular frequency of an operation clock of the photoelastic phase modulator, p is 0 or 1, and t is a time;

the control/analysis unit acquires output signals of the two-dimensional detector obtained by the sequential production of the two kinds of measuring beams calculates $S_{3S}$ by the equation $S_{3S} = S_{30} - S_{31}$ wherein $S_{30}$ and $S_{31}$ are the output signals corresponding to $M_{3p}$ with p=0 and 1, respectively; and the control/analysis unit calculates, setting $S_{1S}$ to $S_S$, an actual measurement value of $S_{1S}/S_{3S}$, which is a ratio of two sine wave component values $S_{1s}$ and $S_{3s}$; and determines $J_S$, $J_C$, and $J_0(\alpha)$ according to a look-up table obtained by calculation beforehand using a relationship expression represented by $S_{1S}/S_{3S} = J_1(\alpha)/J_3(\alpha)$.

According to a polarization modulation imaging ellipsometer (15) of the invention, in the polarization modulation imaging ellipsometer (1) or (2), the light source unit further comprises a light source that sequentially emits light, and an amplitude modulator that modulates the light emitted from the light source at a predetermined frequency and outputs the modulated light as transmitted light.

According to a polarization modulation imaging ellipsometer (16) of the invention, in the polarization modulation imaging ellipsometer (15), the amplitude modulator is a member selected from the group consisting of acousto-optical elements, electro-optical elements, and liquid crystal filters.

According to a polarization modulation imaging ellipsometer (17) of the invention, in the polarization modulation imaging ellipsometer (15), the light source is a white light source;

the ellipsometer further comprises a monochromator or a narrow bandpass filter which splits the light emitted from the white light source, and inputs light of a predetermined wavelength into the amplitude modulator.

According to a polarization modulation imaging ellipsometer (18) of the invention, in the polarization modulation imaging ellipsometer (1) or (2), the light source unit has a light emitting diode or diode laser, and a power supply capable of periodically changing output voltage; and the power supply drives the light emitting diode or diode laser at a predetermined frequency.

According to a polarization modulation imaging ellipsometer (19) of the invention, in the polarization modulation imaging ellipsometer (1) or (2), the two-dimensional detector is an imaging element using a CCD sensor or CMOS image sensor.

EFFECT OF THE INVENTION

According to the polarization modulation imaging ellipsometer of the invention, ellipsometric parameters can be measured quickly and in two dimensions, and, by analyzing the measurement values, the film thickness and optical properties of a film sample can be obtained as a two-dimensional image. Based on the analysis results, both a qualitative two-dimensional image and a quantitative two-dimensional image can be obtained.

When using an imaging ellipsometer in which the wavelength of the measuring beam can be freely determined to measure a film sample composed of two or more layers, the refractive index and film thickness of each layer can be simultaneously determined using two or more ellipsometric parameters obtained by changing the wavelength.

Using the polarization modulation imaging ellipsometer of the invention, $\Delta$ can be measured with high precision in a wide range of $-180°$ to $180°$.

When an objective lens with magnification power of approximately several tens is added to an emitted-light optical unit, an area measuring about several hundreds of micrometers per side of the surface of a sample can be enlarged to thereby observe the optical properties and film thickness of fine patterns with a resolution in the sub-micrometer range.

Light emitted from a light source unit can be led directly to an incident-light optical unit. When an optical fiber is used, the structure can be simplified and the influence of stray light can be suppressed.

EXPLANATION OF REFERENCE CHARACTERS

Figure 1:
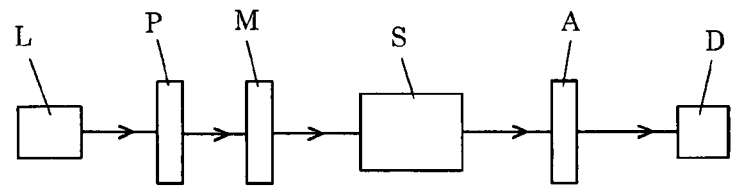
FIG. 1 is a block diagram showing the structure of a PMSA ellipsometer.

L: light source
P: polarizer
M: photoelastic phase modulator (phase modulator)
S: sample
A: analyzer
D: detector
1: light source unit
2: sample holder
3: incident-light optical unit
4: emitted-light optical unit
5: control/analysis unit
6: support member
7: optical fiber
8: signal cable

DETAILED DESCRIPTION OF THE INVENTION

Hereinafter, the present invention will be described according to embodiments. First, polarization modulation imaging ellipsometers will be described theoretically, and then specific polarization modulation imaging ellipsometers will be described.

(1) Principle of the Polarization Modulation Technique

In a PCSA type or PSCA type arrangement, a polarization modulation ellipsometer uses, in place of a compensator C, a photoelastic phase modulator (hereinafter referred to as a phase modulator) that changes the phase of light transmitted therethrough over time. Output signals measured with a single detector are processed using a lock-in amplifier synchronized to the action of the phase modulator, etc., thereby extracting the fundamental wave components, the second harmonic components, etc. From their amplitude intensity, ellipsometric parameters $\Psi$ and $\Delta$ can be determined.

FIG. 1 is a block diagram showing the construction of a PMSA type ellipsometer having a polarizer P, a phase modulator M, a sample S, and an analyzer A arranged in this order. L indicates a light source, and D indicates a detector. When constructed as shown in FIG. 1, light intensity I(t) detected with a detector D is expressed by the following equation.

$$I(t)=I_0\{I_{DC}+I_S \sin[\delta(t)]+I_C \cos[\delta(t)]\} \quad (3)$$

where t represents time, $I_0$ is a coefficient dependent on the reflectivity or transmittance of a sample and the transmittance of an optical element, and $\delta(t)$ represents a phase difference.

Ellipsometric parameters $\Psi$ and $\Delta$ of the sample S, and azimuths P, M, and A of the polarizer P, the phase modulator M, and the analyzer A, respectively, are all defined at $-180°$ to $180°$. However, according to the nature of the trigonometric function, ellipsometric parameters at two angles with a difference whose absolute value is $180°$ have the same value with unlike signs. Therefore, needless to say, the following explanations for the case where the angle is within the range of $0°$ to $180°$ can also be easily applied to the case of an angle within the range of $-180°$ to $0°$.

$I_{DC}$, $I_S$, and $I_C$ represent the direct-current component of the light intensity, the amplitude intensity of the sine wave component, and the amplitude intensity of the cosine wave component, respectively. They can be expressed by the following equations (4a) to (4c).

$$I_{DC} = (1 - \cos 2\psi \cos 2A) + \cos 2(P - M)\cos 2M(\cos 2A - \cos 2\psi) + \qquad (4a)$$
$$\sin 2A \cos \Delta \cos 2(P - M)\sin 2\psi \sin 2M$$

$$I_S = \sin 2(P - M)\sin 2A \sin 2\psi \sin \Delta \qquad (4b)$$

$$I_C = \sin 2(P - M)[(\cos 2\psi - \cos 2A)\sin 2M + \sin 2A \cos 2M \sin 2\psi \cos \Delta] \qquad (4c)$$

The construction may also be a PSMA type having a polarizer P, a sample S, a phase modulator M, and an analyzer A arranged in this order between a light source L and a detector D. In this case, the light intensity detected with the detector is expressed by equations as with equations (4a) to (4c) with P and A interchanged, and equation (3). Although the following explains only a PMSA type for easier understanding, it can be applied to a PSMA type as well using this relation.

When measuring with the polarization modulation technique, the azimuths of the phase modulator M, the polarizer P, and the analyzer A are set so as to suit probable polarization characteristics of the sample and achieve the highest precision. The azimuth of the phase modulator M is usually set at 0°, or at a multiple of 45° or 90°. This simplifies the equations that express $I_{DC}$, $I_S$, and $I_C$, facilitating the analysis. With respect to the azimuths of the polarizer P and the analyzer A, an intermediate value may be the most suitable for some samples.

When M=0°, 90° or 180°, $$I_{DC}=1-(\cos 2P+\cos 2A)\cos 2\Psi+\cos 2P \cos 2A \qquad (5a)$$

$$I_S=(\pm)\sin 2P \sin 2A \sin 2\Psi \sin \Delta \qquad (5b)$$

$$I_C=\sin 2P \sin 2A \sin 2\Psi \cos \Delta \qquad (5c)$$

where (±) is "+1" when the azimuth M is 0° or 180°, and is "−1" when it is 90°.

When M=45° or 135°, $$I_{DC}=(1-\cos 2\Psi \cos 2A)+\sin 2A \cos \Delta \sin 2P \sin 2\Psi \qquad (6a)$$

$$I_S=(\pm)\cos 2P \sin 2A \sin 2\Psi \sin \Delta \qquad (6b)$$

$$I_C=-\cos 2P(\cos 2\Psi-\cos 2A) \qquad (6c)$$

where (±) is "−1" when azimuth M is 45°, and is "+1" when it is 135°.

Light that has been transmitted through the phase modulator M undergoes time-dependent changes in the phase difference between p polarization and s polarization. Here, the change is expressed by a pure sine function of the time, specifically, the following equation.

$$\delta(t)=\alpha \sin \omega t \qquad (7)$$

where ω represents an angular frequency. Amplitude intensity α, which indicates the maximum phase difference, is a function of the driving voltage of the phase modulator M and the wavelength of the light. The cosine and sine functions of δ(t) given in equation (3) can be expanded into the following equations (8) and (9), respectively, with infinite series involving a Bessel function.

$$\cos \delta(t) = \cos(\alpha \sin \omega t) \qquad (8)$$
$$= J_0(\alpha) + 2\sum_{m=1}^{\infty} J_{2m}(\alpha)\cos(2m\omega t)$$

-continued $$\sin \delta(t) = \sin(\alpha \sin \omega t) \qquad (9)$$
$$= 2\sum_{m=0}^{\infty} J_{2m+1}(\alpha)\sin[(2m+1)\omega t]$$

where $J_m(\alpha)$ is the mth-order Bessel function of the first kind with α as an argument. Substituting equations (8) and (9) into equation (3) gives the following equation.

$$I(t) = I_0 I_{DC} + I_0 I_C J_0(\alpha) + 2I_0 I_C \sum_{m=1}^{\infty} [J_{2m}(\alpha)\cos(2m\omega t)] + \qquad (10)$$
$$2I_0 I_S \sum_{m=0}^{\infty} \{J_{2m+1}(\alpha)\sin[(2m+1)\omega t]\}$$

In an ordinary measurement using a single detector, the direct-current components, the fundamental wave components, the second harmonic components, etc., are extracted from output signals of the detector expressed by equation (10) using a lock-in amplifier synchronized to the oscillation of the phase modulator, etc. From their amplitude, ellipsometric parameters Ψ and Δ can be determined.

(2) Parallel Synchronous Detection in Polarization Modulation Imaging Ellipsometer As described above, when a CCD is used as a detector, a measuring beam is intermittently directed at a sample at the same frequency as that of the phase modulator action, thereby extracting Ψ- and Δ-containing items from the signals and thus achieving lock-in detection as in the case of a single detector.

1) Fundamental Principle

As described above, light that has been transmitted through a phase modulator undergoes time-dependent changes in the phase difference between p polarization and s polarization, and the intensity of such light is expressed by equation (10). This may be regarded as a Fourier series with a factor involving a Bessel function as a coefficient, and can be rewritten into the following equation (11).

$$I(t) = a_0 + 2\sum_{m=1}^{\infty} a_m \cos(m\omega t + \varphi_m) \qquad (11)$$

where $a_0=I_0[I_{DC}+I_C J_0(\alpha)]$; when m is an odd number of 1 or more, $a_m=I_0 I_S J_m(\alpha)$ and $\varphi_m=-\pi/2$; and when m is an even number of 2 or more, $a_m=I_0 I_C J_m(\alpha)$ and $\varphi_m=0$.

Here, the measuring beam is amplitude modulated by a modulation signal represented by a Fourier series, having the same fundamental frequencies as those of the measured signals. The modulation signal is expressed by the following equation (12).

$$M(t) = b_0 + 2\sum_{m=1}^{\infty} b_m \cos(m\omega t + \psi_m) \qquad (12)$$

Upon amplitude modulation, the phase of the modulation signal is changed by 1/(a multiple of 2) of the fundamental period over one cycle. Accordingly, optical signals $I_M(t)$ that reach the detector are each expressed as the product of the original signal I(t) and a modulation signal M(t+p/2Pf) having a phase difference as above, by the following equation (13).

$$I_M(t) = I(t)M(t+p/2Pf) \quad (13)$$

where upper-case P is an integer, lower-case p is an integer from 0 to 2P−1, and f represents frequency. The signals $I_M(t)$ that have received 2P kinds of modulation corresponding to different phase differences are stored in a sequential CCD as electric charges, and read out as output signals. The storage time of the CCD is sufficiently longer than the action of the phase modulator, and the output signals thus equal the value obtained by integrating the signals $I_M(t)$ over the storage time. The output signals $S_p$ of the CCD expressed by the following equation (14) can thus be obtained.

$$S_p = \int_0^{KT_0} I_M(t) dt \quad (14)$$
$$= KT_0 a_0 b_0 + 2KT_0 \sum_{m=1}^{\infty} a_m b_m \cos\left(2\pi \frac{pm}{2P} + \psi_m - \varphi_m\right)$$

where $T_0$ represents the fundamental period of the phase modulator, and K represents the periodicity within the storage time of the CCD.

The direct-current components, sine wave components, and cosine wave components contained in the measuring beam are extracted using the output signals of the detector expressed by equation (14), and from their amplitude, ellipsometric parameters Ψ and Δ can be determined.

2) First Detection Method by Intermittent Measuring Beam

Figure 2:
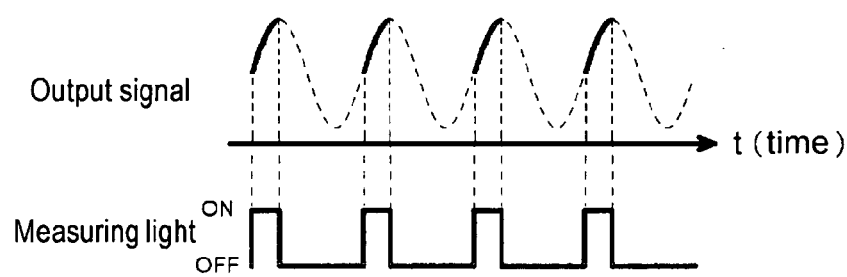
FIG. 2 is a timing chart for a method of interrupting a measuring beam to be used in a polarization modulation imaging ellipsometer according to an embodiment of the present invention.

First, the following explains a method for obtaining ellipsometric parameters (Ψ, Δ) by intermittently directing a measuring beam at a sample at the same frequency as that of the phase modulator action, thereby amplitude modulating the measuring beam. As shown in the lower part of FIG. 2, the measuring beam is intermitted with an ON duration of ¼ cycle (duty ratio: 25%). The upper part of FIG. 2 illustrates output signal waves resulting from the ON and OFF of the measuring beam. This operation is equivalent to the modulation of signal light that has been transmitted through the phase modulator M with a square wave M(t) expressed by the following equation.

$$M(t) = \frac{1}{4} + \frac{2}{\pi} \sum_{m=1}^{\infty} \frac{\sin(m\pi/4)}{m} \cos(m\omega t) \quad (15)$$

Figure 3:
FIG. 3 is a timing chart for a method of delaying time when intermitting a measuring beam to be used in a polarization modulation imaging ellipsometer according to an embodiment of the present invention.
Figure 3:
Figure 3:
Figure 3:
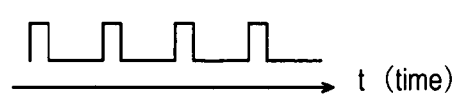

As shown in FIG. 3, for the intermittent measuring beam, four time lags, i.e., 0, ¼, ½ and ¾ cycle, are provided relative to the operation clock of the phase modulator M. Specifically, the measuring beam I(t) incident on the detector D is subjected to the sequential modulation by square waves M(t+p/4f) having the phase differences, as expressed by the following equation.

$$I_M(t) = I(t)M(t+p/4f) \quad (16)$$

where p is an integer from 0 to 3, and f represents frequency. Measuring beam $I_M(t)$ that has received four kinds of modulation corresponding to difference phase differences is stored in a sequential CCD as electric charges, and read out as output signals. The storage cycle in the CCD is sufficiently longer than the action of the phase modulator, so the output signals equal the time average of $I_M(t)$. Output signals $S_p$ (p=0, 1, 2, 3) of the CCD expressed by the following equation can thus be obtained.

$$S_{p=0,1,2,3} = \frac{1}{4} KT_0 I_0 [I_{DC} + I_C J_0(\alpha)] + \quad (17)$$
$$\frac{2}{\pi} KT_0 I_0 I_C \sum_{m=1}^{\infty} \left[ \frac{J_{2m}(\alpha)}{2m} \sin(m\pi/2)\cos(mp\pi) \right] -$$
$$\frac{2}{\pi} KT_0 I_0 I_S \sum_{m=0}^{\infty} \left\{ \frac{J_{2m+1}(\alpha)}{2m+1} \sin[(2m+1)\pi/4]\sin[(2m+1)p\pi/2] \right\}$$

The linear combination of the output signals is computed to extract the items containing Ψ and Δ. This gives the following equations (18) to (20).

$$S_S = S_3 - S_1 = KT_0 I_0 I_S J_S \quad (18)$$
$$S_C = S_0 - S_1 + S_2 - S_3 = KT_0 I_0 I_C J_C \quad (19)$$
$$S_{DC} = S_0 + S_1 + S_2 + S_3 = KT_0 I_0 [I_{DC} + I_C J_0(\alpha)] \quad (20)$$

$S_S$, $S_C$, and $S_{DC}$ may be regarded as the sine wave components, cosine wave components, and direct-current components of output signals of the CCD, respectively. $J_S$ and $J_C$ are defined by the following equations (21) and (22), respectively.

$$J_S = \frac{4}{\pi} \sum_{m=0}^{\infty} \left\{ (-1)^m \frac{J_{2m+1}(\alpha)}{2m+1} \sin[(2m+1)\pi/4] \right\} \quad (21)$$

$$J_C = \frac{8}{\pi} \sum_{m=0}^{\infty} \left[ (-1)^m \frac{J_{4m+2}(\alpha)}{4m+2} \right] \quad (22)$$

Therefore, using the above equations (18) to (22), the storage time $KT_0$ of the CCD and the coefficient $I_0$ that relates to the reflectivity or transmittance of the sample S and the transmittance of the optical element can be removed, giving the equations such as the following (23) and (24).

$$R_S = S_S / S_{DC} = \frac{I_S J_S}{I_{DC} + I_C J_0(\alpha)} \quad (23)$$

$$R_C = S_C / S_{DC} = \frac{I_C J_C}{I_{DC} + I_C J_0(\alpha)} \quad (24)$$

Equations (23) and (24) each have an infinite series involving a zero-order Bessel function with the amplitude intensity α of the phase modulator M as an argument and a first- or grater-order Bessel function; however these can be calibrated as described below. As shown in equations (4) to (6), $I_{DC}$, $I_S$, and $I_C$ are functions of ellipsometric parameters Ψ and Δ. This thus establishes a simultaneous equation containing two unknowns, and the solution of this equation determines Ψ and Δ. In this way, by intermitting a measuring beam in synchronization with the action of the phase modulator, ellipsometric parameters Ψ and Δ can be determined from the output signals of the CCD.

3) Second Detection Method by Intermittent Measuring Beam

The following explains a method for obtaining ellipsometric parameters (Ψ, Δ) by intermitting a measuring beam to thereby amplitude modulate the measuring beam, thereby detecting sine wave and cosine wave components in the same manner as described above, except that the components are not collectively detected as above but are individually detected followed by integration of the data.

First, the measuring beam is intermitted with an ON duration of ½ cycle (duty ratio: 50%) to detect the sine wave component. In this case, the modulated beam is expressed by the following equation (25).

$$M(t) = \frac{1}{2} + \frac{2}{\pi}\sum_{m=0}^{\infty}\frac{1}{2m+1}\sin[(2m+1)\omega t] \tag{25}$$

For the intermittent measuring beam, when two time lags, i.e., 0 and ½ cycle, are provided relative to the operation clock of the phase modulator M, the measuring beam $I_M(t)$ incident on the detector is expressed by the following equation.

$$I_M(t) = I(t)M(t+p/2f) \tag{26}$$

where p is 0 or 1. Electric charges in response to the measuring beam $I_M(t)$ that has received two kinds of modulation corresponding to different phase differences are alternately stored in the CCD, and read out as output signals. This gives output signals $S_p$ (p=0, 1) of the CCD expressed by the following equation.

$$S_{p=0,1} = \frac{1}{2}KT_0I_0[I_{DC}+I_CJ_0(\alpha)] + \frac{2}{\pi}KT_0I_0I_S\sum_{m=0}^{\infty}\left[\frac{J_{2m+1}(\alpha)}{2m+1}(-1)^p\right] \tag{27}$$

The linear combination of output signals is expressed by the following equations (28) and (29).

$$S_S = S_0 - S_1 = KT_0I_0I_SJ_S \tag{28}$$

$$S_{DC} = S_0 + S_1 = KT_0I_0[I_{DC}+I_CJ_0(\alpha)] \tag{29}$$

Here, $J_S$ is defined by the following equation.

$$J_S = \frac{4}{\pi}\sum_{m=0}^{\infty}\frac{J_{2m+1}(\alpha)}{2m+1} \tag{30}$$

Accordingly, from equations (28) to (30), the following equation can be obtained.

$$R_S = S_S/S_{DC} = \frac{I_SJ_S}{I_{DC}+I_CJ_0(\alpha)} \tag{31}$$

Subsequently, measurement to detect the cosine wave component is performed by successively generating a measuring beam with an ON duration of ¼ cycle and another measuring beam having an opposite phase with an ON duration of ¾ cycle. The modulated beam with an ON duration of ¼ cycle (duty ratio: 25%) is expressed by equation (15), and the modulated beam having an opposite phase with an ON duration of ¾ cycle (duty ratio: 75%) is expressed by the following equation.

$$M(t) = \frac{3}{4} - \frac{2}{\pi}\sum_{m=1}^{\infty}\frac{\sin(m\pi/4)}{m}\cos(m\omega t) \tag{32}$$

When the modulated beams having duty ratios of 25% and 75% are defined as $M_0(t)$ and $M_1(t)$, respectively, the measuring beam I(t) incident on the detector is expressed by the following equation.

$$I_M(t) = I(t)M_p(t) \tag{33}$$

where p is 0 or 1. Electric charges in response to the measuring beam $I_M(t)$ that has received two kinds of modulation corresponding to different duty ratios are alternately stored in the CCD, and read out output signals. This gives output signals $S_0$ and $S_1$ of the CCD expressed by the following equations.

$$S_0 = \frac{1}{4}I_0[I_{DC}+I_CJ_0(\alpha)] + \frac{2}{\pi}I_0I_C\sum_{m=1}^{\infty}\left[\frac{J_{2m}(\alpha)}{2m}\sin(m\pi/2)\right] \tag{34}$$

$$S_1 = \frac{3}{4}I_0[I_{DC}+I_CJ_0(\alpha)] - \frac{2}{\pi}I_0I_C\sum_{m=1}^{\infty}\left[\frac{J_{2m}(\alpha)}{2m}\sin(m\pi/2)\right] \tag{35}$$

The linear combination of output signals is expressed by the following equations (36) and (37).

$$S_C = (3S_0 - S_1)/2 = KT_0I_0I_CJ_C \tag{36}$$

$$S_{DC} = S_0 + S_1 = KT_0I_0[I_{DC}+I_CJ_0(\alpha)] \tag{37}$$

Here, $J_C$ is defined by the following equation.

$$J_C = \frac{4}{\pi}\sum_{m=0}^{\infty}\left[(-1)^m\frac{J_{4m+2}(\alpha)}{4m+2}\right] \tag{38}$$

Therefore, from equations (28) to (30), the following equation can be obtained.

$$R_C = S_C/S_{DC} = \frac{I_CJ_C}{I_{DC}+I_CJ_0(\alpha)} \tag{39}$$

In this way, individual detections of the sine wave components and cosine wave components of output signals of the CCD gave values $R_S$ and $R_C$ corresponding thereto, respectively, as equations (31) and (39). These equations have the same form as equations (23) and (24) derived from the above corrective detection of the sine wave and cosine wave components. Accordingly, Ψ and Δ can be determined from these equations. Further, a combination of different measuring beams individually detects the sine wave components and cosine wave components, and by successively repeating such operations, both the sine wave component and cosine wave component can be simultaneously measured in real-time.

Successively performing the measurements of either the sine wave or the cosine wave components is also effective. When Ψ or Δ of the sample S is already known, the other parameter can be obtained using equation (31) or equation (39). Further, when Ψ or Δ of the sample S can be regarded as constant, relative changes of the other parameter can be obtained using equation (31) or equation (39). According to this method, because two kinds of light are used, measurement can be performed twice as fast as a collective detection of sine wave and cosine wave components using four kinds of light.

4) Detection Method with Amplitude Modulation of the Measuring Beam Using an Analog Signal When a measuring beam directed at a sample is amplitude modulated using an analog signal having the same fundamental frequency as that of the phase modulator action, $\Psi$- and $\Delta$-containing items can be extracted from the output signals of the CCD as when a measuring beam is intermitted, achieving lock-in detection as in the case of a single detector In this case, modulation signals having the same fundamental frequency as that of the measured signal, represented by a Fourier series with Q as the maximum harmonic order, are used. The modulation signal is expressed by the following equation (40).

$$M(t) = b_0 + 2\sum_{m=1}^{Q} b_m \cos(m\omega t + \psi_m) \tag{40}$$

This amplitude modulation can be achieved by varying the intensity of the measuring beam with a liquid crystal filter that is capable of rapidly changing the transmission. It may also be achieved, using a light-emitting diode or diode laser as a light source, by driving such a light source by an analog signal.

Upon amplitude modulation, the phase of the modulation signal is changed by 1/(a multiple of 2) of the fundamental period over one cycle. Optical signals $I_M(t)$ that reach the detector are each expressed as the product of the original signal I(t) and a modulation signal M(t+p/2Pf) having a phase difference as above, by the following equation (41).

$$I_M(t)=I(t)M(t+p/2Pf) \tag{41}$$

Upper-case P is an integer, and has to be equal to or greater than the maximum harmonic order Q contained in the modulation signal. Lower-case p is an integer from 0 to 2P−1, and f represents frequency. The signals $I_M(t)$ that have received 2P kinds of modulation corresponding to different phase differences are stored in a sequential CCD as electric charges, and read out as output signals. The storage time of the CCD is sufficiently longer than the action of the phase modulator, so the output signals equal the value obtained by integrating the signals $I_M(t)$ over the storage time. Output signals $S_p$ of the CCD expressed by the following equation (42) can thus be obtained.

$$S_P = \int_0^{KT_o} I_M(t)dt \tag{42}$$
$$= KT_0 a_0 b_0 + 2KT_0 \sum_{m=1}^{Q} a_m b_m \cos\left(2\pi\frac{pm}{2P} + \psi_m - \varphi_m\right)$$

The maximum harmonic order contained in an output signal is equal to the highest harmonic contained in a modulation signal. This is because the product of sine waves of different frequencies becomes zero after integration, removing higher order harmonic components that were contained in the original signal. Further, according to Shannon's sampling theorem, when the maximum harmonic order contained in the target signal is defined as Q, and P is an integer equal to or greater than Q, the signal can be reproduced completely by sampling 2P or more signal values at regular intervals over one cycle of the fundamental wave. Therefore, from the 2P kinds of output signals $S_p$ based on the modulation signal with phase shifts at regular intervals over one cycle of the fundamental period, the intensity of the direct-current components contained in the signals $I_M(t)$, the intensity and the phase of the fundamental wave, and the intensity and the phase of all harmonics can be obtained. That is, the discrete Fourier transform as expressed by equation (43) and equation (44) may be performed.

$$X_r = \frac{1}{2PKT_0}\sum_{p=0}^{2P-1} S_p \cos 2\pi\frac{pr}{2P} \tag{43}$$

$$Y_r = \frac{1}{2PKT_0}\sum_{p=0}^{2P-1} S_p \sin 2\pi\frac{pr}{2P} \tag{44}$$

The computation results are as follows.

$$r=0 X_0=a_0 b_0 Y_0=0 \tag{45}$$

$$r<P X_r=a_r b_r \cos(\Psi_r-\Psi_r) Y_r=a_r b_r \sin(\phi_r-\Psi_r) \tag{46}$$

$$r=P X_p=2a_p b_p \cos(\Psi_r-\Psi_r) Y_p=0 \tag{47}$$

As expressed in equation (11), light that has been transmitted through the phase modulator contains higher order harmonics. However, the phase thereof is constant, and is $-\pi/2$ in the case of the fundamental wave and odd harmonics, and 0 in the case of even harmonics. To obtain ellipsometric parameters, it is sufficient to determine the intensity of the direct-current component, the fundamental wave component, and the second harmonic component. Therefore, when an integer equal to or greater than the maximum harmonic order contained in the target signal is defined as P, measurement is performed using 2P or more kinds of modulation signals with phase shifts, and the above technique of numeric processing using the discrete Fourier transform is simplified as follows.

The first instance is where signals expressed by the following equation obtained by synthesizing the fundamental wave having the same fundamental frequency as that of the phase modulator with a second harmonic are used as modulation signals. Specifically, the four kinds having the phase delayed by ¼ of the wavelength of the fundamental wave, which are expressed by the following equation (48), are used.

$$M_p(t)=1+2\cos[\omega(t+p/4f)-\pi/2]+2\cos[2\omega(t+p/4f)] \tag{48}$$

where p is an integer from 0 to 3. As a result, the output signals $S_p$ of the CCD are expressed by the following equation (49).

$$S_p=KT_0 a_0+2KT_0[a_1 \cos(\pi p/2)+a_2 \cos(\pi p)] \tag{49}$$

The linear combination of output signals is computed in order to obtain ellipsometric parameters. This gives in the following equations (50) to (52).

$$S_S=S_0-S_2=4KT_0 a_1=4KT_0 I_0 I_S J_1(\alpha) \tag{50}$$

$$S_C=S_0-S_1+S_2-S_3=8KT_0 a_2=8KT_0 I_0 I_C J_2(\alpha) \tag{51}$$

$$S_{DC}=S_0+S_1+S_2+S_3=4KT_0 a_0=4KT_0 I_0[I_{DC}+I_C J_0(\alpha)] \tag{52}$$

$S_S$, $S_C$, and $S_{DC}$ are the sine wave components, cosine wave components, and direct-current components of output signals of the CCD, respectively. Except the prefactor containing the storage time $KT_0$ of the CCD, these equations are the same as in the measurement using a single detector followed by detection and data processing using a lock-in amplifier, etc. Therefore, ellipsometric parameters $\Psi$ and $\Delta$ can be determined using a known method from the above-shown direct-current components, fundamental wave components, and second harmonics.

When $J_S=J_1(\alpha)$ and $J_C=2J_2(\alpha)$, the above equations can be modified as follows.

$$S_S=4KT_0I_0I_SJ_S \quad (53)$$

$$S_C=4KT_0I_0I_CJ_C \quad (54)$$

$$S_{DC}=4KT_0I_0[I_{DC}+I_CJ_0(\alpha)] \quad (55)$$

These equations are the same as in the amplitude modulation by intermitting a measuring beam, except that the prefactor is fourfold. Further, the prefactor and the coefficient $I_0$ that relates to the reflectivity or transmittance of the sample S and the transmittance of the optical element can be removed, giving the following equations (56) and (57).

$$R_S = S_S/S_{DC} = \frac{I_SJ_S}{I_{DC}+I_CJ_0(\alpha)} \quad (56)$$

$$R_C = S_C/S_{DC} = \frac{I_CJ_C}{I_{DC}+I_CJ_0(\alpha)} \quad (57)$$

Further, based on a fundamental wave having the same fundamental frequency as that of the phase modulator and the second harmonic, four kinds of signals having the phase delayed by ¼ wavelength of the fundamental wave, which are expressed by the following equations, may also be used as modulation signals.

$$M_{1p}(t)=1+2\cos[\omega(t+p/4f)-\pi/2] \quad (58)$$

$$M_{2p}(t)=1+2\cos[2\omega(t+p/4f)] \quad (59)$$

where p is 0 or 1. Consequently, output signals $S_p$ of the CCD are as follows.

$$S_{1p}=KT_0a_0+2KT_0a_1\cos(\pi p) \quad (60)$$

$$S_{2p}=KT_0a_0+2KT_0a_2\cos(\pi p) \quad (61)$$

The linear combination of output signals is computed in order to obtain the ellipsometric parameters. This gives the following equations (62) to (65).

$$S_S=S_{10}-S_{11}=4KT_0a_1=4KT_0I_0I_SJ_1(\alpha) \quad (62)$$

$$S_{DC}=S_{10}+S_{11}=2KT_0a_0=2KT_0I_0[I_{DC}+I_CJ_0(\alpha)] \quad (63)$$

$$S_C=S_{20}-S_{21}=4KT_0a_2=4KT_0I_0I_CJ_2(\alpha) \quad (64)$$

$$S_{DC}=S_{20}+S_{21}=2KT_0a_0=2KT_0I_0[I_{DC}+I_CJ_0(\alpha)] \quad (65)$$

where $S_S$, $S_C$, and $S_{DC}$ are the sine wave components, cosine wave components, and direct-current components of output signals of the CCD. As with the above, except the prefactor containing the storage time $KT_0$ of the CCD, these equations are the same as in measurement and data processing using a single detector, a lock-in amplifier, etc. When $J_S=2J_1(\alpha)$ and $J_C=2J_2(\alpha)$, the above equations can be modified as follows.

$$S_S=2KT_0I_0I_SJ_S \quad (66)$$

$$S_C=2KT_0I_0I_CJ_C \quad (67)$$

$$S_{DC}=2KT_0I_0[I_{DC}+I_CJ_0(\alpha)] \quad (68)$$

Further, as with the above, equations (56) and (57) can be obtained.

5) Effect of the Static Phase Difference in the Phase Modulator

The above description is based on the assumption that the phase difference in the measuring beam caused by the phase modulator M can be expressed by a pure sine function as shown in equation (7). However, the phase modulator may cause a slight phase difference (static phase difference) $\delta_0$ in the transmitted light even when no voltage is applied. Using such a phase modulator, when a voltage is applied, the phase difference in the measuring beam is expressed by the following equation.

$$\delta(t)=\alpha\sin\omega t+\delta_0 \quad (69)$$

Using $\cos\delta_0 \approx 1$ derived from $\delta_0 \ll 1$, sine and cosine functions of $\delta(t)$ given in equations (3) and (7) can be modified to the following equations (70) and (71).

$$\sin[\delta(t)] = \sin(\alpha\sin\omega t + \delta_0) = \sin(\alpha\sin\omega t) + \cos(\alpha\sin\omega t)\sin\delta_0 \quad (70)$$

$$\cos[\delta(t)] = \cos(\alpha\sin\omega t + \delta_0) = \cos(\alpha\sin\omega t) - \sin(\alpha\sin\omega t)\sin\delta_0 \quad (71)$$

Accordingly, the light intensity in the detector is generally expressed by the following equation.

$$I(t) = I_0\{I_{DC} + (I_S - I_C\sin\delta_0)\sin(\alpha\sin\omega t) + (I_C + I_S\sin\delta_0)\cos(\alpha\sin\omega t)\} \quad (72)$$

In order to detect the sine wave and cosine wave components by the parallel synchronous detection method, as in the above, using, as a modulation signal, a square wave having the same fundamental frequency as that of the phase modulator M or a composite wave of a sine wave with a harmonic thereof, predetermined time lags are provided relative to the operation clock of the phase modulator M, and sequential modulation is applied thereto. The output signal of the CCD corresponding to each is then computed. The sine wave components $S_S$, cosine wave components $S_C$, and direct-current components $S_{DC}$ of output signals of the CCD are thereby obtained as follows.

$$S_S=A_SI_0(I_S-I_C\sin\delta_0)J_S \quad (73)$$

$$S_C=A_CI_0(I_C+I_S\sin\delta_0)J_C \quad (74)$$

$$S_{DC}=S_0+S_1=A_{DC}I_0[I_{DC}+(I_C+I_S\sin\delta_0)J_0(\alpha)] \quad (75)$$

$A_S$, $A_C$, and $A_{DC}$ are prefactors, and are the products of the storage time $KT_0$ of the CCD with a predetermined integer that varies depending on the technique. For equations (23) and (24) or equations (31) and (39), the following equations (76) and (77) can be obtained.

$$R_S = \frac{(I_S-I_C\sin\delta_0)J_S}{I_{DC}+(I_C+I_S\sin\delta_0)J_0(\alpha)} \quad (76)$$

$$R_C = \frac{(I_C+I_S\sin\delta_0)J_C}{I_{DC}+(I_C+I_S\sin\delta_0)J_0(\alpha)} \quad (77)$$

(3) Calibration of the Device Characteristics for a Polarization Modulation Imaging Ellipsometer 1) Calibration Considerations Similarly to the case where signals from a single detector are analyzed using a lock-in amplifier, etc., when a CCD detector is used for detection, the sine wave components, cosine wave components, and direct-current components can be extracted in real-time from the output signals. Further, determination of the ratio thereof can partly eliminate factors caused by the device characteristics. However, these equations still contain a zero-order Bessel function including the amplitude intensity of the phase modulator as an argument and infinite-series factor involving a first- or grater-order Bessel functions, as well as in the phase modulator. In order to measure a static phase difference re the ellipsometric parameters of the sample in real-time, these factors need to be calibrated prior to the measurement using the sample.

This is a problem associated with the characteristics of phase modulators, which is peculiar to polarization modulation ellipsometers. There is also a problem in common with other types of ellipsometers, that is, a problem of error in the azimuth of an optical element, which is caused by disagreement between the azimuth orientation of the optical element and the scale marked on the optical element holder. Calibration methods for polarization modulation ellipsometers using a single detector have been established (see the above nonpatent documents 2 and 3). The extinction ratio of commercial optical measuring polarizers is generally extremely large, and such polarizers and analyzers may be regarded as having ideal characteristics. One optical element that causes deficiencies in the characteristics for ellipsometers is a compensator, but this is not generally used in polarization modulation ellipsometers.

Parallel rays having a certain area are directed at a sample, and light that has been reflected from or transmitted through each point on the surface of the sample is detected with a CCD microsensor corresponding to each pixel of the two-dimensional data (i.e., each of two-dimensionally arranged photo diodes). The phase modulator M has an aperture having a certain area, and the characteristics thereof are generally not uniform over the entire aperture. Particularly, the deviation of the amplitude intensity of the phase modulator M from the value at the center is known to increase with an increase in distance from the center of the aperture.

According to data from Hinds Instruments, Inc., a United States manufacturer that specializes in phase modulators, with respect to an element with an effective aperture diameter of 16 mm, an aperture diameter having 90% or more of the amplitude intensity is 16 mm, and an aperture diameter having 99% or more the amplitude intensity is 9 mm. Accordingly, when using an aperture diameter of 9 mm or less for measurement, the amplitude intensity within the observed area may be regarded as almost constant. However, when using a larger aperture diameter for measurement, for the output signals from a CCD microsensor corresponding to each point in the aperture, calibration of the above factors is required.

Calibration of the device characteristics is generally performed with a linear arrangement (angle of incidence: 90°) obtained by rotating the optical system to linearly arrange an incident-light optical unit and an emitted-light optical unit. The incidence angle thus differs greatly between the actual measurement and the calibration. When the sample is in a reflective arrangement, a measuring beam that has been transmitted through the phase modulator is horizontally (right-left) reversed when it is reflected from the surface of the sample. However, if the surface of the sample is flat as seen in a broad perspective, except the above right-left reversal, the cross-sectional shape of the measuring beam remains unchanged before and after reflection. Therefore, when the sample surface that reflects the measuring beam is maintained at a fixed position, this enables, between the actual measurement and calibration, an almost constant correspondence between the position in the aperture of the phase modulator and the position of the measured surface of the CCD.

A standard sample used for calibration has ellipsometric parameters that are stable and almost uniform within the sample plane. Therefore, when the correspondence between the position in the aperture of the phase modulator and the position of the measured surface of the CCD is almost constant between the actual measurement and calibration, the measurement values can be calibrated for each pixel of the two-dimensional data by using the values obtained in the calibration experiment.

Further, a zero-order Bessel function including the amplitude intensity of the phase modulator as an argument and the infinite-series factor involving a first- or grater-order Bessel function, as well as the static phase difference in the phase modulator, are theoretically independent of the constants or set values of optical elements such as the phase modulator M, the polarizer P, and the analyzer A. Therefore, the setting of these optical elements may differ between the calibration and the actual measurement. Although the azimuths of the polarizer P and the analyzer A are sometimes intermediate values as described above, in the calibration, in order to facilitate the analysis, the azimuths of the polarizer P and the analyzer A are preferably 0° or a multiple of 45° or 90°.

Needless to say, prior to the calibration of the device characteristics peculiar to ellipsometers, the positions of all components forming the optical system are calibrated. Specifically, adjustments are made so that the center of a luminous flux from the light source passes through the center of the collimator, polarizer, phase modulator, and analyzer that form the optical system.

2) Calibration of the Azimuths of Optical Elements

The following explains a method for calibrating errors in setting the azimuths of the polarization modulation imaging ellipsometer. This method can also be applied to an ideal phase modulator without any static phase difference and also to a phase modulator having a static phase difference.

The true azimuths of the polarizer, the phase modulator, and the analyzer are defined as P, M, and A, respectively, and the azimuth values indicated on the scales shown on the element holders are defined as P', M', and A'. To calibrate the element azimuths, a sample having ellipsometric parameters as close as possible to $[\Psi, \Delta]=[45°(135°), 90°]$ is used. However, precise values may remain unidentified. Parameters of $30°<\Psi<60°$ or $120°<\Psi<150°$ and $70°<\Delta<110°$ are preferable, and $40°<\Psi<50°$ or $130°<\Psi<140°$ and $80°<\Delta<100°$ are more preferable.

First, in order to calibrate M and A to be M=0° and A=0°, P' is set at P'=45°. M' and A' are repeatedly adjusted so that the average values of the sine wave components $S_S$ and cosine wave components $S_C$ of the output signals of the CCD in the aperture are both 0. Next, to calibrate P to be P=0°, M' and A' are set at $M'=0°+M_0$ and $A'=45+A_0$. P' is adjusted so that the average values of the sine wave components $S_S$ and cosine wave components $S_C$ of the output signals of the CCD in the aperture are both 0.

In the case of a phase modulator having a static phase difference $\delta_0$, $S_S$ is expressed by equation (73) and has a zero-order dependence on (i.e., direct relation to) the sine wave component $I_S$ [equation (4b)] of the light intensity, and a first-order dependence on (i.e., proportional relation to, with $\delta_0$ being the coefficient) the cosine wave component $I_C$ [equation (4c)]. $S_C$ is expressed by equation (74), and has zero-order and first-order dependences on $I_C$ and $I_S$, respectively. Accordingly, M and A need to be adjusted simultaneously and repeatedly. Further, by simultaneously and repeatedly adjusting $S_S$ and $S_C$ to be 0, a highly accurate calibration can be achieved.

In the case of an ideal phase modulator without any static phase difference, $S_S$ is expressed by equation (18) or (28), and $S_C$ is expressed by equation (19) or (36). $S_S$ and $S_C$ have an individual zero-order dependence on $I_C$ and $I_S$, respectively, and thus can be independently adjusted.

The true azimuths of the polarizer, phase modulator, and analyzer can thus be expressed as follows.

$$P = P' - P_0 \tag{78a}$$

$$M = M' - M_0 \tag{78b}$$

$$A = A' - A_0 \tag{78c}$$

$P_0$, $M_0$, and $A_0$ are each a value indicated when the true azimuth of the element is 0°, obtained from the above calibration.

3) Setting the Amplitude Intensity of the Phase Modulator and Calibrating Static Phase Difference The amplitude intensity $\alpha$ of the phase modulator M is a function of the driving voltage and the light wavelength. For commercially available phase modulators, such a relation is predetermined, and generally, input of the amplitude intensity and the wavelength automatically sets a suitable driving voltage. When the setting is $\alpha = 137.8°$, a zero-order Bessel function is $J_0(\alpha) = 0$. Even in the case of a first- or greater-order Bessel function, or when $J_S$ and $J_C$ are an infinite-series factor involving a Bessel function, computation can be easily performed using the value of $\alpha$. The above adjustment for the value of the zero-order Bessel function can suppress, to a certain degree, crosstalk between the sine wave components, cosine wave components and direct-current components obtained by the parallel synchronous detection method, thereby improving accuracy.

For a phase modulator having a static phase difference $\delta_0$, calibration is necessary. Therefore, commercially available phase modulators are provided with an aperture diameter $\phi$ having 99% or more the amplitude intensity. However, the aperture diameter herein is approximately 80% or less $\phi$, and a circular area homocentric to the circular area of the aperture diameter $\phi$ is used. The aperture diameter is sufficiently small to allow the values of $J_0(\alpha)$, $J_S$, and $J_C$ to be uniform over the entire aperture diameter. Subsequently, measurement is performed using a sample having known $\Psi$ and $\Delta$ as a standard sample S between a phase modulator M and an analyzer A. Equations (76) and (77) are simplified with the above relation $J_0(\alpha) = 0$, as follows.

$$R_S^{cal,av} = \frac{(I_S^{cal} - I_C^{cal}\sin\delta_0)J_S}{I_{DC}^{cal}} \tag{79}$$

$$R_C^{cal,av} = \frac{(I_C^{cal} + I_S^{cal}\sin\delta_0)J_C}{I_{DC}^{cal}} \tag{80}$$

The superscript "cal" attached to $R_S$, $R_C$, $I_{DC}$, $I_S$, and $I_C$ indicates that it is a calibration value, while the superscript "av" attached to $R_S$ and $R_C$ indicates that it is an average value for the entire aperture diameter. $J_S$ and $J_C$ can be computed from the set amplitude intensity $\alpha$ as described above, and accordingly, after measurement using the standard sample S, the static phase difference $\delta_0$ can be determined by applying equation (79) or (80). The static phase difference $\delta_0$ may be regarded as uniform in the aperture diameter, and an average value in the aperture diameter can be reasonably used as a calibration value. When measurement at a plurality of wavelengths is required, the above calibration is performed at each wavelength.

The following describes standard samples that are often used, together with $I_{DC}$, $I_S$, and $I_C$ therefor. In the following instances, the optical systems are all in a linear arrangement. The computation is based on equation (4), but may also be performed based on equation (5) or (6).

No sample ($\Psi = 45°$, $\Delta = 0°$):

$$I_{DC} = 1 + \cos 2(P-M)\cos 2M \cos 2A + \sin 2A \cos 2(P-M) \sin 2M \tag{81a}$$

$$I_S = 0 \tag{81b}$$

$$I_C = -\sin 2(P-M) + \sin 2A \cos 2M \sin 2\Psi \cos \Delta - \cos 2A \sin 2M \tag{81c}$$

Compensator (quarter-wave plate), azimuth 90° ($\Psi = 45°$, $\Delta = 90°$):

$$I_{DC} = 1 \tag{82a}$$

$$I_S = \sin 2(P-M)\sin 2A \tag{82b}$$

$$I_C = -\sin 2(P-M)\cos 2A \sin 2M \tag{82c}$$

Polarizer, azimuth 0° ($\Psi = 0°$, $\Delta = 0°$):

$$I_{DC} = (1 - \cos 2A) + \cos 2(P-M)\cos 2M(\cos 2A - 1) \tag{83a}$$

$$I_S = 0 \tag{83b}$$

$$I_C = \sin 2(P-M)(1 - \cos 2A)\sin 2M \tag{83c}$$

Polarizer, azimuth 90° ($\Psi = 90°$, $\Delta = 0°$):

$$I_{DC} = 1 + \cos 2(P-M)\cos 2M \cos 2A + \sin 2A \cos 2(P-M) \sin 2M \tag{84a}$$

$$I_S = 0 \tag{84b}$$

$$I_C = -\sin 2(P-M)(1 + \cos 2A)\sin 2M \tag{84c}$$

4) Calibration of the Amplitude Intensity of a Phase Modulator

When measurement is performed with an aperture diameter having 99% or more of the amplitude intensity as described for commercially available phase modulators, the amplitude intensity of the phase modulator may be regarded as uniform in the aperture diameter, and measurement can be performed based on the set amplitude intensity. However, it is difficult to completely align the centers of the measuring beam and the phase modulator, and this requires a reduction of the aperture diameter to be used to approximately 80% or less. When use of a larger aperture diameter is required, or when highly accurate measurement with 99% or more of the amplitude intensity is necessary, the amplitude intensity of the phase modulator is calibrated at each point in the aperture diameter for which the measurement is performed.

Therefore, as in the calibration of the static phase difference in the phase modulator, measurement is performed using a sample having known $\Psi$ and $\Delta$ installed as a standard sample S between a phase modulator M and an analyzer A. In the case of an ideal phase modulator with no static phase difference, the following relation exists.

$$R_S^{cal} = \frac{I_S^{cal} J_S}{I_{DC}^{cal} + I_C^{cal} J_0(\alpha)} \quad (85)$$

$$R_C^{cal} = \frac{I_C^{cal} J_C}{I_{DC}^{cal} + I_C^{cal} J_0(\alpha)} \quad (86)$$

In the case of a phase modulator with a static phase difference, the following relation exists.

$$R_S^{cal} = \frac{(I_S^{cal} - I_C^{cal}\sin\delta_0) J_S}{I_{DC}^{cal} + (I_C^{cal} + I_S^{cal}\sin\delta_0) J_0(\alpha)} \quad (87)$$

$$R_C^{cal} = \frac{(I_C^{cal} + I_S^{cal}\sin\delta_0) J_C}{I_{DC}^{cal} + (I_C^{cal} + I_S^{cal}\sin\delta_0) J_0(\alpha)} \quad (88)$$

The method for computing $I_{DC}^{cal}$, $I_S^{cal}$, and $I_C^{cal}$ are as described for the calibration of the static phase difference.

Three unknowns, $J_S$, $J_C$, and $J_0(\alpha)$, exist in the above equations (85) and (86), or equations (87) and (88). To define $J_0(\alpha)$, the above measurement should be performed at least twice using samples with different $\Psi$ and $\Delta$ as standard samples S. $R_S^{cal}$ and $R_C^{cal}$ expressed by the above equations (85) and (86) or equations (87) and (88), respectively, can be simultaneously obtained by one measurement, and two measurements thus give four equations in total. This eliminates the unknowns $J_S$ and $J_C$, determining $J_0(\alpha)$. The zero-order Bessel function $J_0(\alpha)$ is a monotone decreasing function of the amplitude intensity $\alpha$, and therefore, using a look-up table obtained by calculating the relation therebetween in advance, $\alpha$ can be easily obtained from $J_0(\alpha)$. Accordingly, the measurement value of the amplitude intensity $\alpha$ at each point in the aperture diameter can be easily obtained.

As descried above, although the amplitude intensity of the phase modulator is almost uniform near the center, it decreases with an increase in distance from the center.

In the case of a phase modulator that uses an element plate cut into a regular octagon, assuming that the central position is $(x_0, y_0)$, the value of $\alpha$ at the center is $\alpha_0$, and the distance from the center where $\alpha=0$ is $r_0$, the amplitude intensity $\alpha$ can be expressed as a function of the position $(x, y)$ in the aperture, by the following equation.

$$\alpha = \alpha_0 \cos\left\{\frac{\pi}{2}\frac{[(x-x_0)^2 + (y-y_0)^2]^{1/2}}{r_0}\right\} \quad (89)$$

In the case of a phase modulator that uses an element plate cut into a rectangle, assuming that the height at the center in the minor axis direction is $y_0$, the value of $\alpha$ at the center is $\alpha_0$, and the distance from the center where $\alpha=0$ is $r_0$, the amplitude intensity $\alpha$ can be expressed as a function of the longitudinal height y by the following equation.

$$\alpha = \alpha_0 \cos\left(\frac{\pi}{2}\frac{|y-y_0|}{r_0}\right) \quad (90)$$

Commercially available phase modulators are provided with an aperture diameter with 99% or more of the amplitude intensity and 90% or more of the amplitude intensity. Although the relation between the distance from the center and the amplitude intensity is likely to vary for each element, data regarding this are generally not attached.

To reduce the noise in the actual measurement, the calibration values of the amplitude intensity in a circular area, whose diameter is the aperture diameter, desirably have rational and smooth distribution. Therefore, fitting is performed to equation (89) or (90) using the above-adjusted $\alpha_0=137.8°$ and the above-obtained amplitude intensity value $\alpha$ at each point in the circular area whose diameter is the aperture diameter. In the case of equation (89), fitting is performed to two-dimensional data using the value of $\alpha$ to thereby determine the three unknown parameters $x_0$, $y_0$, and $r_0$. In the case of equation (90), one-dimensional fitting is performed using data obtained by averaging the distribution of $\alpha$ at the same height y in a direction x to thereby determine the two unknown parameters $y_0$ and $r_0$. The calibration values of the amplitude intensity $\alpha$ at each point of the aperture are thus determined.

(4) Real-Time Correction of Variation in the Amplitude Intensity of a Phase Modulator In the above description, the amplitude intensity of a phase modulator M does not change with time, and the $J_S$, $J_C$, $J_0(\alpha)$ values that have been determined in the calibration process are constant during measurement. However, it is known that the amplitude intensity will change depending on the wavelength of the light to be measured and the measurement temperature. Temperature dependency can be controlled to some extent, but not completely, by precisely controlling the temperature of the element.

It is known that, with a single detector, variation in the amplitude intensity of a phase modulator can be corrected in real-time by using a lock-in amplifier and the like to measure a third harmonic wave component in addition to the direct-current component, fundamental wave component, and second harmonic component (Non-Patent Document 10). As is clear from equation (10), since the third harmonic wave component has the same coefficient "$2I_0I_S$" as that of the fundamental wave component, the ratio of the fundamental harmonic wave component to the third wave component is equal to the ratio of the first order Bessel function to the third order Bessel function, i.e., $J_1(\alpha)/J_3(\alpha)$. This value is a function of the amplitude intensity $\alpha$ of a phase modulator, and has no correlation with the ellipsometric parameters of the sample. The amplitude intensity $\alpha$ is generally adjusted to 137.8° in which $J_0(\alpha)$ is equal to 0 ($J_0(\alpha)=0$). When $\alpha$ is equal to such a value, the ratio $J_1(\alpha)/J_3(\alpha)$ varies by about 2.3% when the $\alpha$ value changes by 1°. This variation can generally be detected easily, and thus the variation in the infinite-series factor and in the $J_0(\alpha)$ value caused by the change in the $\alpha$ value can be corrected.

Considering the case when the amplitude is modulated by interrupting the measuring beam, which is one of the methods for performing parallel synchronous detection using a CCD, when measurement is performed using four kinds of lights each having an ON duration of ¼ cycle and a time lag of 0, ¼, ½, and ¾ cycle, respectively, the output signal of the CCD is expressed by equation (13), and when measurement is performed using two kinds of lights each having an ON duration of ½ cycle and a time lag of 0 and ½ cycle, respectively, the output signal of the CCD is expressed by equation (27). According to these two equations, the amplitude variation caused by the change in the $\alpha$ value can be corrected by utilizing the fact that the coefficients of the sine wave components of the time-average outputs of the CCD are different.

First, measurement is performed using two kinds of lights each having an ON duration of ¼ cycle and a time lag of ¼ cycle and ¾ cycle, respectively, and the first sine wave component value $S_{S1}$ expressed by equation (18) is calculated. Subsequently, measurement is performed using two kinds of lights each having an ON duration of ½ cycle and a time lag of 0 cycle and ½ cycle, respectively, and the second sine wave component value $S_{S2}$ expressed by equation (28) is calculated. Thus, the ratio of these two sine wave component values can be calculated according to the following equation.

$$S_{S1}/S_{S2} = \frac{\sum_{m=0}^{\infty}\left\{(-1)^m \frac{J_{2m+1}(\alpha)}{2m+1}\sin[(2m+1)\pi/4]\right\}}{\sum_{m=0}^{\infty}\frac{J_{2m+1}(\alpha)}{2m+1}} \quad (91)$$

In the case where the α value is 137.8°, the $S_{S1}/S_{S2}$ ratio varies by about 0.65% when the α value changes by 1°. This variation can generally be detected easily, and thus the variation in the infinite-series factor and in the $J_0(\alpha)$ value caused by the change in the α value can be corrected.

Next, the actual measurement procedures will be described. In order to determine an ellipsometric parameter, measurement is performed using four kinds of lights each having an ON duration of ¼ cycle and a time lag of 0, ¼, ½, and ¾ cycle, respectively, thereby obtaining the output signals of the CCD expressed by equations (18) to (20). Alternatively, measurement is performed using two kinds of lights each having an ON duration of ½ cycle and a time lag of 0 and ½, respectively, thereby obtaining the output signals of the CCD expressed by equations (28) to (29). Thus, according to the normal measurement, the first sine wave component value $S_{S1}$ is calculated by the former procedure, and the second sine wave component value $S_{S2}$ is calculated by the latter procedure. Therefore, in order to perform real-time correction of the infinite-series factor and the $J_0(\alpha)$ value using changes in the α value, measurement using two kinds of lights each having an ON duration of ½ cycle and a time lag of 0 and ½, respectively, is performed following the normal measurement in the former procedure, thereby yielding the second sine wave component value $S_{S2}$. In the latter procedure, measurement using two kinds of lights each having an ON duration of ¼ cycle and a time lag of ¼ and ¾, respectively, is performed following the normal measurement in the latter procedure, thereby yielding the first sine wave component value $S_{S1}$.

With respect to the second sine wave component value $S_{S2}$, equation (27) used for the calculation contains only the direct-current component in addition to the sine wave component. Therefore, measurement is performed using either one of two lights each having an ON duration of ½ cycle and a time lag of 0 cycle and ½ cycle, respectively, and the average signal of the CCD is obtained. Then, the direct-current component value $S_{DC}$ expressed by equation (16) and obtained by the normal measurement in the former procedure is subtracted from the average signal of the CCD, thereby obtaining $S_{S2}$. Since five kinds of lights are used in total for measurement, measurement can be performed at a greater speed.

Since $S_{S1}/S_{S2}$ is a monotonically decreasing function of amplitude intensity α, the relationship between $S_{S1}/S_{S2}$ and the infinite-series factors $J_S$, $J_C$, and $J_0(\alpha)$ can be obtained by calculation beforehand. For example, with reference to a look-up table that has been produced in advance by calculation, $J_S$, $J_C$, and $J_0(\alpha)$ can be quickly determined from the $S_{S1}/S_{S2}$ value obtained by measurement.

The variation in the α value over time does not need to be corrected for the entire aperture diameter of the phase modulator. For example, $S_{S1}/S_{S2}$ values are measured in an area near the aperture center where about 1% to about 5% of the total pixels are included, and the average $S_{S1}/S_{S2}$ value for this area can then be used as a correction value. Assuming that the α values are uniform within the aperture diameter, it is preferable to perform the measurement using the average value as a correction value. When the distribution of the α values within the aperture diameter needs to be determined, it is preferable to calculate the correction value of α at each point in the aperture using the average value and the above parameters obtained by fitting.

Using the parallel synchronous detection method in which the amplitude of the measuring beam is modulated using an analog signal, each harmonic component can be extracted. Therefore, real-time correction can be performed in a similar manner to ordinary synchronous detection methods using a single detector, lock-in amplifier, etc.

The actual measurement procedures will now be described. As described above, the direct-current component, fundamental wave component, and second harmonic component can be obtained by using, as a modulation signal, a synthesized signal composed of the fundamental wave and the second harmonic wave that have the same fundamental frequency as that of the phase modulator, or by using the waves individually. In order to obtain the third harmonic component, in addition to these procedures, two kinds of signals based on a third harmonic wave having the same fundamental frequency as that of the phase modulator are used as a modulation signal. The phase of each of the two signals is delayed by ⅙ of the wavelength of the fundamental wave, as expressed by the following equations.

$$M_{3p}(t)=1+2\cos[3\omega(t+p/6f)-\pi/2] \quad (92)$$

Where p is 0 or 1. The output signal Sp of the CCD is as follows.

$$S_{3p}=KT_0 a_0+2KT_0 a_3\cos(p\pi) \quad (93)$$

The linear combination of these output signals is as follows.

$$S_{S3}=S_{30}+S_{31}=4KT_0 a_3=4KT_0 I_S J_3(\alpha) \quad (94)$$

$$S_{DC}=S_{30}+S_{31}=2KT_0 a_0=2KT_0 I_0[I_{DC}+I_C J_0(\alpha)] \quad (95)$$

Since the third harmonic component has the same coefficient "$4KT_0 I_0 I_S$" as that of the fundamental wave component, the ratio of the fundamental wave component to the third harmonic component is equal to the ratio of the first order Bessel function to the third order Bessel function, $J_1(\alpha)/J_3(\alpha)$ similar to the case where a single detector is used. Specifically, the relationship is expressed by the following equation.

$$S_{S1}/S_{S3}=J_1(\alpha)/J_3(\alpha)$$

This value is a function of the amplitude intensity α of the phase modulator, and the function has no correlation with the ellipsometric parameters of the sample. When the amplitude intensity α is equal to 137.8°, the $J_1(\alpha)/J_3(\alpha)$ ratio varies by about 2.3% when the α value changes by 1°. This variation can generally be detected easily, and thus the variation in the infinite-series factor and in the $J_0(\alpha)$ value caused by the change in the α value can be corrected. Since $J_1(\alpha)/J_3(\alpha)$ is a monotonically decreasing function of amplitude intensity α, $J_0(\alpha)$, $J_1(\alpha)$, and $J_2(\alpha)$ can be quickly determined from the $S_{S1}/S_{S3}$ value obtained by measurement when the relationship obtained by calculation in advance is provided as a corresponding look-up table.

As described above, since the amplitude intensity α also depends on the wavelength of the light, it needs to be calibrated for each wavelength. Some methods have been proposed to achieve efficient measurement at several wavelengths using single detector. The Non-Patent Document 11 discloses a method comprising experimentally measuring the applied voltages and wavelengths that satisfies the condition in which $J_0(α)$ is equal to 0, approximating the obtained data by a cubic polynomial, and automatically adjusting the applied voltage according to the measuring wavelength. The above-mentioned Non-Patent Document 10 discloses a method for automatically adjusting an applied voltage in such a manner that the amplitude intensity α remains constant by monitoring the $J_1(α)/J_3(α)$ value. When parallel synchronous detection is performed with a CCD, in the same manner as in the correction of the variation in the amplitude intensity α over time, the variation in the infinite-series factor and in the $J_0(α)$ value caused by the change in a measurement wavelength can be corrected by monitoring the $S_{S1}/S_{S2}$ value obtained by intermitting the measuring beam or the $S_{S1}/S_{S3}$ value obtained by modulating the amplitude of the measuring beam with an analog signal. The above methods are useful in cases where a commercially available phase modulator, which can automatically adjust the applied voltage to match a wavelength, cannot be installed in an ellipsometer for a particular application.

(5) Polarization Modulation Imaging Ellipsometer

Figure 4:
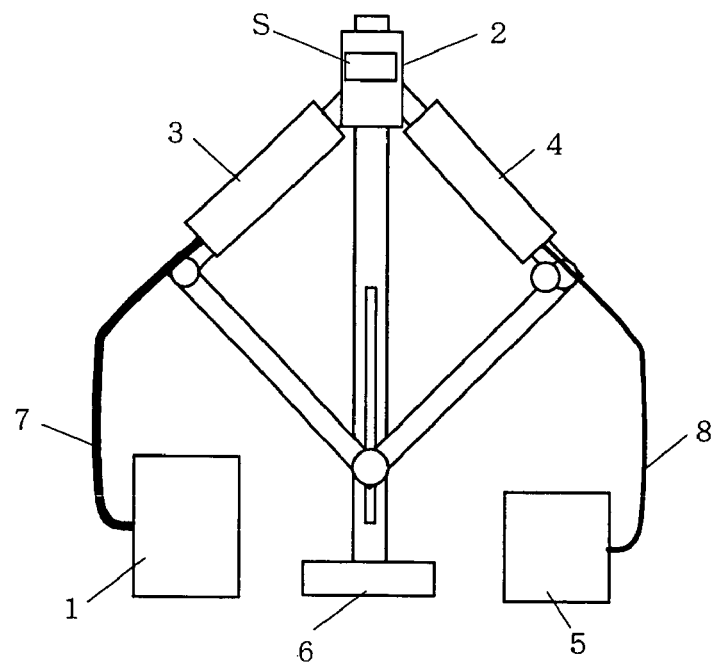
FIG. 4 is an elevation view showing a vertical-type polarization modulation imaging ellipsometer according to an embodiment of the present invention.
Figure 5:
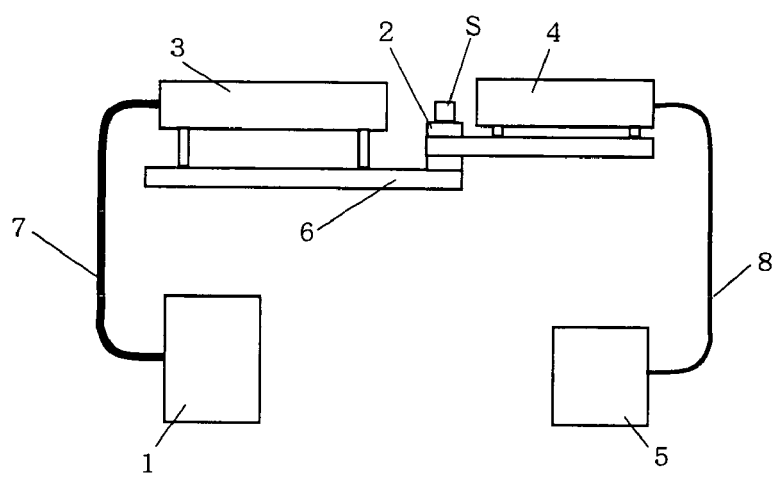
FIG. 5 is an elevation view showing a horizontal-type polarization modulation imaging ellipsometer according to an embodiment of the present invention.

As shown in FIG. 4, a polarization modulation imaging ellipsometer according to an embodiment of the invention has a light source unit 1, a sample holder 2, an incident-light optical unit 3, an emitted-light optical unit 4, a control/analysis unit 5, a support member 6, an optical fiber 7 that transmits a light from the light source unit 1 to the incident-light optical unit 3, and signal cable 8 that transmits an electrical signal that is output by the emitted-light optical unit 4 to the control/analysis unit 5. The layout of the elements is not limited to the vertical arrangement shown in FIG. 4, and the elements may be arranged horizontally as shown in FIG. 5.

The light source unit 1 has a light source that continuously emits light. When measurement is performed while intermitting the measuring beam, the light source has an acousto-optical element or an electro-optical element (neither is shown) that can intermit transmitted light at an arbitrary frequency ranging from about several tens of kHz to about 100 kHz. When measurement is performed while modulating the amplitude of the measuring beam using an analog signal, the light source has an element (liquid crystal filter and the like) that can modulate an input light at an arbitrary frequency ranging from about several tens of kHz to about 100 kHz and can output the modulated light as a transmitted light. Such amplitude modulating elements penetrate a light from the light source as it is or while condensing the light by using a lens with an effective aperture diameter ranging from several millimeters to several centimeters. The light source unit 1 may have a light emitting diode or diode laser, and a power supply capable of changing the output voltage periodically. The light emitting diode or diode laser may be driven at a frequency ranging from several tens of kHz to several hundreds of kHz by the power supply. The wavelength of a measuring beam may be made variable by separating the light from a white light source by using a monochromator or a narrow bandpass filter.

The incident-light optical unit 3 has a collimator, a polarizer, and a phase modulator (neither is shown). Light from the light source unit 1 is modulated by a phase modulator, so the phase difference between p polarized light and s polarized light varies sinusoidally. The operation of intermitting or blinking the measuring beam is synchronized with the operation of the phase modulator in frequency and phase. The measuring beam thus modulated is directed to the measuring plane of a sample S placed on a sample holder 2.

The emitted-light optical unit 4 has an analyzer and a two-dimensional detector such as a CCD or the like (neither is shown). Light that has been reflected from or transmitted through the sample is analyzed by the emitted-light optical unit 4 to determine its polarization state and then transmitted to the control/analysis unit 5 after being converted into an electrical signal.

The control/analysis unit 5 controls a phase modulator and an amplitude modulation element, such as an acousto-optical element, electro-optical element, liquid crystal filter, or the like, or a cyclic voltage generator, and drives them at the same frequency while providing a regular phase difference. The control/analysis unit 5 analyzes the output signal of the CCD, and calculates at high speed the ellipsometric parameters in each pixel of an image corresponding to each point of the sample surface that is being observed by the CCD. The sample holder 2 fixedly supports the sample S to establish the inclination. The support member 6 supports the sample holder 2, incident-light optical unit 3, and emitted-light optical unit 4, and is manually or automatically adjusted so that the angles of the incident-light optical unit 3 and the emitted-light optical unit 4 are adjusted to a predetermined angle and so that an incident light is reflected from or transmitted through the surface of the sample S that is placed in the sample holder 2, and the light that is projected from the sample is emitted to the emitted-light optical unit 4.

Figure 6:
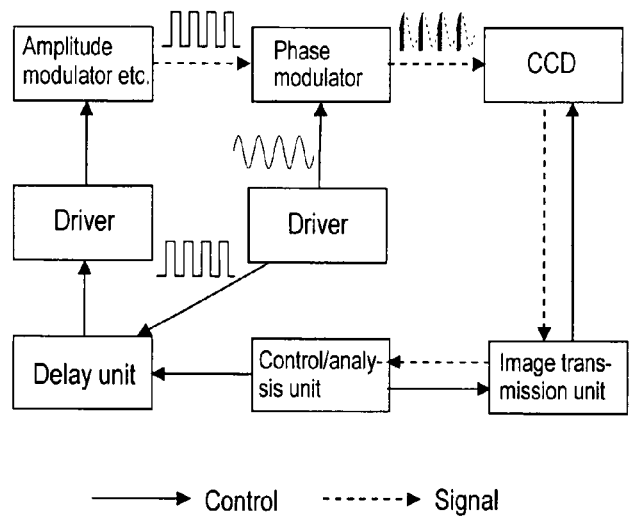
FIG. 6 is a block diagram showing the flow of control by the control/analysis unit 5 and a measurement signal according to an embodiment of the present invention.

FIG. 6 is a block diagram showing the flow of control by the control/analysis unit 5 and the measurement signal. The specification describes the case where the measuring beam is intermitted, and a sine wave component and a cosine wave component are collectively detected while the ON duration is set to ¼ cycle. It is a matter of course that the following description may be applied to the case where a sine wave component and a cosine wave component are individually detected and the amplitude of the measuring beam is modulated using an analog signal. The phase modulator of the emitted-light optical unit 4 is driven at a frequency ranging from several tens of kHz to several hundreds of kHz. A clock generated by the driver is used as the master clock for the entire system. A time delay unit produces a square wave with a ¼-cycle duration ON timing synchronized with the master clock. With this timing, the phase differences are shifted one after another by 0, ¼, ½, and ¾ cycle by the control/analysis unit 5. The acousto-optical element or electro-optical element, or the light emitting diode or laser diode, is driven using this square wave, thereby periodically intermitting or blinking the measuring beam. The measuring beam is modulated by a phase modulator that operates at a constant frequency and phase. Then, the modulated measuring beam is reflected from the sample surface and is detected with the CCD through an analyzer. Thus, four images each corresponding to one of the four phase differences are obtained.

Figure 7:
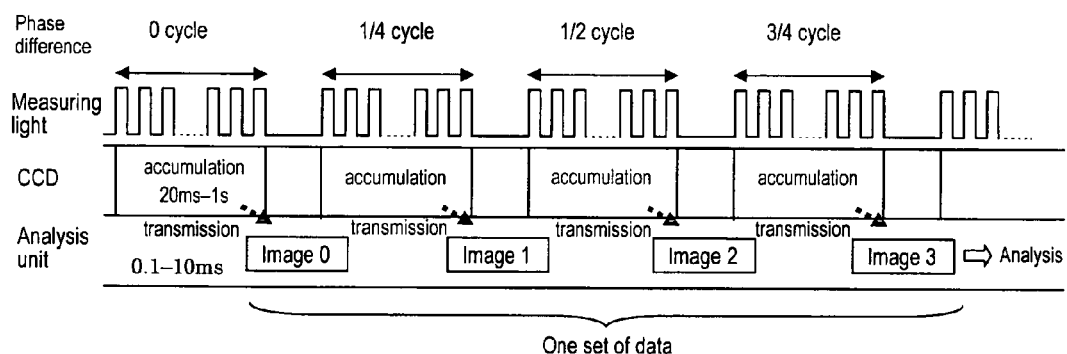
FIG. 7 is a timing chart showing the time relationship among the pulse strings of a measuring beam having four phase differences, the storage of signal light in a CCD, and the transfer of data according to an embodiment of the present invention.

FIG. 7 shows a timing chart indicating the time relationship among the pulse strings of a measuring beam having four phase differences, the accumulation of signal light in the CCD, and the transfer of data. The CCD is open-gated, the pulse string of a measuring beam is generated, and an electric charge corresponding to the signal light is stored in the CCD. The charges (data) are transferred in batches to the analysis unit after being stored for a predetermined period (about 20 milliseconds to 1 second). In this way, four images corresponding to the pulse strings of a measuring beam whose phase is shifted by ¼ cycle are obtained. Ellipsometric parameters for each pixel can be obtained by performing operations among the pixel data of these obtained images according to the above-mentioned equations, to determine the ellipsometric parameters as a two-dimensional image.

For these operations, equations (23) and (24), or equations (31) and (39), are used when assuming an ideal phase modulator M, and, in the case of a phase modulator having a static phase difference $\delta_0$, equations (23) and (24) are used. The azimuths of the polarizer, phase modulator, and analyzer are each calibrated by adjusting the sine wave component and cosine wave component of the output signal of the CCD. The amplitude intensity α of the phase modulator is set to 137.8°, at which the zero-order Bessel function ($J_0(\alpha)$) becomes 0, and the values of infinite-series factors $J_S$ and $J_C$ containing a first- or grater-order Bessel function are calculated. The static phase difference of the phase modulator is determined using equation (79) or (80) after performing measurement using a standard sample whose Ψ and Δ are predetermined. When calibrating the amplitude intensity within the aperture diameter of the phase modulator, equations (85) and (86) are used after the measurement is performed using two or more standard samples. In the case of a phase modulator having a static phase difference $\delta_0$, equations (87) and (88) are used. Alternatively, a value obtained by fitting the above-described measurement result to a relationship expression (89) or (90) between the position within the aperture diameter of the phase modulator and the corresponding amplitude intensity is used as a calibration value.

When a commonly used type of CCD is used to acquire the image of one field by an external trigger, about 10 milliseconds is required for data transmission and other processing in addition to the integration time in the CCD. In contrast, when 1,000 pulses are integrated, the integration time becomes 20 milliseconds. Thus, the shortest time required for obtaining four images to determine coefficients T and A for ellipsometry becomes 120 milliseconds. When a high-speed CCD is used, the shortest time required for data transmission and other processing becomes 0.1 millisecond or less. Thus, the measurement time can be further shortened under conditions where the pulse count and integration time are the same.

The invention claimed is:

1. A polarization modulation imaging ellipsometer comprising:
   a light source unit that emits light whose amplitude periodically changes at a predetermined frequency;
   a sample holder on which a sample is placed;
   an incident-light optical unit having a collimator, a polarizer, and a photoelastic phase modulator which modulates light emitted from the light source unit to sinusoidally vary a phase difference between a p polarized light and an s polarized light of the light and applies the light to a measurement plane of the sample placed on the sample holder;
   an emitted-light optical unit having an analyzer which analyzes a polarization state of light that has been reflected from or transmitted through the sample and a two-dimensional detector which converts light received from the analyzer to an electrical signal and outputs the electrical signal;
   a control/analysis unit which operates the light source unit and the photoelastic phase modulator at the same frequency in a range of several tens of kHz to several hundreds of kHz, and to which an output signal emitted from the two-dimensional detector is input; wherein
   the polarizer, the photoelastic phase modulator, the sample, and the analyzer are arranged in this order on a light path, resulting in a PMSA type (polarizer-modulator-sample-analyzer) arrangement;
   the light source unit sequentially produces a measuring beam having a predetermined time lag relative to an operation clock of the photoelastic phase modulator; and
   the control/analysis unit calculates ellipsometric parameters Ψ and Δ for each pixel of a two-dimensional image of a surface of the sample to be observed with the two-dimensional detector using an output signal of the two-dimensional detector under conditions (1) to (3):
   (1) amplitude intensity of light that has passed through the photoelastic phase modulator being expressed as "α", an mth order Bessel function of the first kind being expressed as $J_m(\alpha)$ in which m is an integer equal to or greater than 0 and the amplitude intensity α is a variable, a factor containing $J_m(\alpha)$ in which m is an odd number being expressed as $J_S$, and a factor containing $J_m(\alpha)$ in which m is an even number being expressed as $J_C$;
   (2) a direct-current component of light intensity detected by the detector being expressed as $I_{DC}$, amplitude intensity of a sine wave component of light intensity detected by the detector being expressed as $I_S$, and amplitude intensity of a cosine wave component of light intensity detected by the detector being expressed as $I_C$, azimuths of the polarizer, photoelastic phase modulator, and analyzer being expressed as P, M, and A, respectively, and $I_{DC}$, $I_S$, and $I_C$ being represented by $$I_{DC} = (1 - \cos 2\Psi \cos 2A) + \cos 2(P - M)\cos 2M(\cos 2A - \cos 2\Psi) +$$
$$\sin 2A \cos \Delta \cos 2(P - M)\sin 2\Psi \sin 2M$$
$$I_S = \sin 2(P - M)\sin 2A \sin 2\Psi \sin \Delta$$
$$I_C = \sin 2(P - M)[(\cos 2\Psi - \cos 2A)\sin 2M + \sin 2A \cos 2M \sin 2\Psi \cos \Delta];$$

(3) a sine wave component of the output signal of the two-dimensional detector being expressed as $S_S$, a cosine wave component of the output signal of the two-dimensional detector being expressed as $S_C$, a direct-current component of the output signal of the two-dimensional detector being expressed as $S_{DC}$, and $R_S = S_S/S_{DC}$ and $R_C = S_C/S_{DC}$; wherein
   when the photoelastic phase modulator is ideal, the ellipsometric parameters Ψ and Δ are calculated based on equation 1:

$$R_S = \frac{I_S J_S}{I_{DC} + I_C J_0(\alpha)} \quad \text{[Equation 1]}$$

and $$R_C = \frac{I_C J_C}{I_{DC} + I_C J_0(\alpha)}$$

and when the photoelastic phase modulator has static phase difference $\delta_0$, the ellipsometric parameters Ψ and Δ are calculated based on equation 2:

$$R_S = \frac{(I_S - I_C \sin \delta_0) J_S}{I_{DC} + (I_C + I_S \sin \delta_0) J_0(\alpha)} \quad \text{[Equation 2]}$$

and

-continued $$R_C = \frac{(I_C + I_S \sin\delta_0)J_C}{I_{DC} + (I_C + I_S \sin\delta_0)J_0(\alpha)}.$$

2. A polarization modulation imaging ellipsometer comprising:
a light source unit that emits light whose amplitude periodically changes at a predetermined frequency;
a sample holder on which a sample is placed;
an incident-light optical unit having a collimator and a polarizer;
an emitted-light optical unit having a photoelastic phase modulator which modulates light that has been reflected from or transmitted through the sample to sinusoidally vary a phase difference between a p polarized light and an s polarized light of the light, an analyzer which analyzes the polarization state of light that has been transmitted through the photoelastic phase modulator, and a two-dimensional detector which converts light received from the analyzer into an electrical signal and outputs the electrical signal;
a control/analysis unit which operates the light source unit and the photoelastic phase modulator at the same frequency in a range of several tens of kHz to several hundreds of kHz, and to which an output signal emitted from the two-dimensional detector is input; wherein
the polarizer, the sample, the photoelastic phase modulator, and the analyzer are arranged in this order on a light path, resulting in a PSMA type (polarizer-sample-modulator-analyzer) arrangement;
the light source unit sequentially produces a measuring beam having a predetermined time lag relative to an operation clock of the photoelastic phase modulator; and
the control/analysis unit calculates ellipsometric parameters $\Psi$ and $\Delta$ for each pixel of a two-dimensional image of a surface of the sample to be observed with the two-dimensional detector using an output signal of the two-dimensional detector under conditions (1) to (3):
(1) amplitude intensity of light that has passed through the photoelastic phase modulator being expressed as "$\alpha$", an mth order Bessel function of the first kind being expressed as $J_m(\alpha)$ in which m is an integer equal to or greater than 0 and the amplitude intensity $\alpha$ is a variable, a factor containing $J_m(\alpha)$ in which m is an odd number being expressed as $J_S$, and a factor containing $J_m(\alpha)$ in which m is an even number being expressed as $J_C$;
(2) a direct-current component of light intensity detected by the detector being expressed as $I_{DC}$, amplitude intensity of a sine wave component of light intensity detected by the detector being expressed as $I_S$, and amplitude intensity of a cosine wave component of light intensity detected by the detector being expressed as $I_C$, azimuths of the polarizer, photoelastic phase modulator, and analyzer being expressed as P, M, and A, respectively, and $I_{DC}$, $I_S$, and $I_C$ being represented by $$I_{DC} = (1 - \cos 2\Psi \cos 2P) + \cos 2(A - M)\cos 2M(\cos 2P - \cos 2\Psi) +$$
$$\sin 2P \cos\Delta \cos 2(A - M)\sin 2\Psi \sin 2M$$
$$I_S = \sin 2(A - M)\sin 2P \sin 2\Psi \sin\Delta$$
$$I_C = \sin 2(A - M)[(\cos 2\Psi - \cos 2P)\sin 2M + \sin 2P \cos 2M \sin 2\Psi \cos\Delta];$$

(3) a sine wave component of the output signal of the two-dimensional detector being expressed as $S_S$, a cosine wave component of the output signal of the two-dimensional detector being expressed as $S_C$, a direct-current component of the output signal of the two-dimensional detector being expressed as $S_{DC}$, and $R_S=S_S/S_{DC}$ and $R_C=S_C/S_{DC}$; wherein
when the photoelastic phase modulator is ideal, the ellipsometric parameters $\Psi$ and $\Delta$ are calculated based on equation 3:

$$R_S = \frac{I_S J_S}{I_{DC} + I_C J_0(\alpha)} \quad \text{[Equation 3]}$$

and $$R_C = \frac{I_C J_C}{I_{DC} + I_C J_0(\alpha)}$$

and when the photoelastic phase modulator has static phase difference $\delta_0$, the ellipsometric parameters $\Psi$ and $\Delta$ are calculated based on equation 4:

$$R_S = \frac{(I_S - I_C \sin\delta_0)J_S}{I_{DC} + (I_C + I_S \sin\delta_0)J_0(\alpha)} \quad \text{[Equation 4]}$$

and $$R_C = \frac{(I_C + I_S \sin\delta_0)J_C}{I_{DC} + (I_C + I_S \sin\delta_0)J_0(\alpha)}.$$

3. A polarization modulation imaging ellipsometer according to claim 1 or 2; wherein
the light source unit sequentially produces four kinds of measuring beams, each measuring beam having a rectangular wave in which an ON duration is ¼ cycle and a time lag is 0, ¼, ½, or ¾ cycle relative to an operation clock of the photoelastic phase modulator; and
the control/analysis unit acquires output signals of the two-dimensional detector that are obtained by sequential production of the four kinds of measuring beams each having a time lag of 0, ¼, ½, or ¾ cycle, and the obtained output signals being denoted as $S_0$, $S_1$, $S_2$, and $S_3$ respectively corresponding to time lags of 0, ¼, ½, and ¾ cycle, and calculates $S_S$, $S_C$, and $S_{DC}$ values by the following equations:

$$S_S = S_3 - S_1,$$
$$S_C = S_0 - S_1 + S_2 - S_3, \text{ and}$$
$$S_{DC} = S_0 + S_1 + S_2 + S_3.$$

4. A polarization modulation imaging ellipsometer according to claim 1 or 2; wherein
when the light source unit sequentially produces two kinds of measuring beams, each measuring beam having a rectangular wave in which the ON duration is ½ cycle and a time lag of 0 or ½ cycle relative to an operation clock of the photoelastic phase modulator;
the control/analysis unit acquires output signals of the two-dimensional detector that are obtained by sequential production of the two kinds of measuring beams having time lags of 0 and ½ cycle, and are denoted as $S_0$ and $S_1$, respectively, calculates $S_S$ and $S_{DC}$ values by the following equations:

$$S_S = S_0 - S_1, \text{ and } S_{DC} = S_0 + S_1; \text{ and}$$

when the light source unit sequentially produces a first measuring beam in which the ON duration is ¼ cycle and a second measuring beam whose phase is opposite to that of the first measuring beam and in which the ON duration is ¾ cycle;

the control/analysis unit acquires output signals of the two-dimensional detector that are obtained by sequential production of the first and second measuring beams, and are denoted as $S_2$ and $S_3$, respectively, and calculates $S_c$ and $S_D$ values by the following equations:

$S_c=(3S_2-S_3)/2$, and $S_{DC}=S_3+S_3$.

5. A polarization modulation imaging ellipsometer according to claim 1 or 2; wherein the light source unit sequentially produces four kinds of measuring beams each having an amplitude $M_p$ expressed by the following function:

$M_p(t)=1+2\cos[\omega(t+p/4f-\pi/2)]+2\cos[2\omega(t+p/4f)]$, where f denotes the frequency of an operation clock of the photoelastic phase modulator, ω denotes an angular frequency, p is an integer from 0 to 3, and t is a time; and the control/analysis unit acquires output signals of the two-dimensional detector obtained by sequential production of the four kinds of measuring beams, and calculates $S_S$, $S_C$, and $S_{DC}$ values by the following equations:

$S_S=S_1-S_3$, $S_C=S_0-S_1+S_2-S_3$, and $S_{DC}=S_0+S_1+S_2+S_3$; wherein $S_0$, $S_1$, $S_2$, and $S_3$ are output signals corresponding to p=0, 1, 2, and 3 respectively.

6. A polarization modulation imaging ellipsometer according to claim 1 or 2; wherein the light source unit sequentially produces four kinds of measuring beams each having amplitudes $M_{1p}$ or $M_{2p}$ expressed by functions:

$M_{1p}(t)=1+2\cos[\omega(t+p/4f)-\pi 2]$ and $M_{2p}(t)=1+2\cos[2\omega(t+p/4f)]$; wherein ω denotes angular frequency of an operation clock of the photoelastic phase modulator, p is 0 or 1, and t is a time;

the control/analysis unit acquires output signals of the two-dimensional detector obtained by sequential production of the four kinds of measuring beams, and calculates $S_S$, $S_C$ and $S_{DC}$ values by the following equations:

$S_S=S_{10}-S_{11}$, $S_C=S_{20}-S_{21}$, and $S_{DC}=S_{10}+S_{11}$ or $S_{DC}=S_{20}+S_{21}$, wherein $S_{10}$ and $S_{11}$ are output signals corresponding to $M_{1p}$ with p=0 and 1 respectively, and $S_{20}$ and $S_{21}$ are output signals corresponding to $M_{2p}$ with p=0 and 1 respectively.

7. A polarization modulation imaging ellipsometer according to claim 1 or 2; wherein azimuth indicated by graduation of the polarizer, photoelastic phase modulator, and analyzer is denoted as P', M', and A', respectively;

the control/analysis unit calibrates the P, M, and A using the following equations:

$P=P'-P_0$ $M=M'-M_0$ $A=A'-A_0$, wherein $M_0$ and $A_0$ are values of M' and A', respectively, when an average of each $S_S$ and $S_C$ in an aperture of the photoelastic phase modulator becomes equal to 0 in the case where P'=45° and a sample having ellipsometric parameter Ψ in a range of 30°<Ψ<60° or in a range of 120°<Ψ<150° and ellipsometric parameter Δ in a range of 70°<Δ<110° is used; and $P_0$ is a value of P' when an average of each $S_S$ and $S_C$ in the aperture of the photoelastic phase modulator becomes equal to 0 in the case where M' is equal to 0°+$M_0$, A' is equal to 45°+$A_0$ and a sample having ellipsometric parameter Ψ in a range of 30°<Ψ<60° or in a range of 120°<Ψ<150° and an ellipsometric parameter Δ in a range of 70°<Δ<110° is used.

8. A polarization modulation imaging ellipsometer according to claim 1 or 2; wherein α is 137.8°, which is the value when $J_0(\alpha)$ becomes equal to 0; and $J_S$ and $J_C$ are calculated from the α value.

9. A polarization modulation imaging ellipsometer according to claim 1 or 2; wherein for each wavelength which needs to measured, when the photoelastic phase modulator has a static phase difference $\delta_0$, the control/analysis unit performs measurement using a standard sample, whose ellipsometric parameters are known, and the circular area which is concentric with a circle whose diameter is an aperture diameter of an area having 99% or more of amplitude intensity in the photoelastic phase modulator and whose diameter is 80% or less of the aperture diameter; and the control/analysis unit calculates an average $\delta_0$ in the aperture diameter of the photoelastic phase modulator using equation 5:

$$R_S^{cal,av} = \frac{(I_S^{cal} - I_C^{cal}\sin\delta_0)J_S}{I_{DC}^{cal}} \quad [\text{Equation 5}]$$

$$R_C^{cal,av} = \frac{(I_C^{cal} + I_S^{cal}\sin\delta_0)J_C}{I_{DC}^{cal}}, \text{ wherein}$$

$I_{DC}$, $I_S$, and $I_C$, which have been calculated by substituting the known ellipsometric parameters Ψ and Δ, are denoted as $I_{DC}^{cal}$, $I_S^{cal}$ and $I_C^{cal}$; and averages of calibration values of the $R_S$ and $R_C$ in the circular area whose diameter is the aperture diameter determined using the standard sample are denoted as $R_S^{cal,av}$ and $R_C^{cal,av}$.

10. A polarization modulation imaging ellipsometer according to claim 1 or 2; wherein the control/analysis unit calculates the ellipsometric parameters Ψ and Δ using a measurement result obtained by using a circular area which is concentric with a circle whose diameter is an aperture diameter of an area having 99% or more of amplitude intensity in the photoelastic phase modulator and whose diameter is 80% or less of the aperture diameter and by assuming that amplitude intensity is uniform in the circular area.

11. A polarization modulation imaging ellipsometer according to claim 1 or 2; wherein the control/analysis unit performs measurement using at least two kinds of standard samples having different ellipsometric parameters $\Psi$ and $\Delta$, values of $I_{DC}$, $I_S$, and $I_C$ calculated by substituting known ellipsometric parameters $\Psi$ and $\Delta$ of the standard sample being denoted as $I_{DC}^{cal}$, $I_S^{cal}$, and $I_C^{cal}$, respectively, the values of $R_S$ and $R_C$ measured using the standard sample being denoted as $R_S^{cal}$ and $R_C^{cal}$ respectively;

the control/analysis unit calculates at least two kinds of two formulae represented by the following equations 6 and 7, equation 6 being used when the photoelastic phase modulator is ideal, and equation 7 being used when the photoelastic phase modulator has static phase difference $\delta_0$:

$$R_S^{cal} = \frac{I_S^{cal} J_S}{I_{DC}^{cal} + I_C^{cal} J_0(\alpha)} \quad \text{[Equation 6]}$$

$$R_C^{cal} = \frac{I_C^{cal} J_C}{I_{DC}^{cal} + I_C^{cal} J_0(\alpha)}$$

$$R_S^{cal} = \frac{(I_S^{cal} - I_C^{cal}\sin\delta_0) J_S}{I_{DC}^{cal} + (I_C^{cal} + I_S^{cal}\sin\delta_0) J_0(\alpha)} \quad \text{[Equation 7]}$$

$$R_C^{cal} = \frac{(I_C^{cal} + I_S^{cal}\sin\delta_0) J_C}{I_{DC}^{cal} + (I_C^{cal} + I_S^{cal}\sin\delta_0) J_0(\alpha)}$$

$J_0(\alpha)$ being determined from said at least four formulae; and the control/analysis unit determines amplitude intensity $\alpha$ in each point in an aperture of the photoelastic phase modulator using a look-up table in which a relationship between $\alpha$ and $J_0(\alpha)$ has been calculated in advance.

12. A polarization modulation imaging ellipsometer according to claim 11; wherein when the photoelastic phase modulator is an element plate cut into a regular octagon, the control/analysis unit determines three unknown parameters $x_0$, $y_0$, and $r_0$ by performing fitting the amplitude intensity $\alpha$ measured at each point within the aperture diameter to a formula represented by the following equation:

$$\alpha = \alpha_0 \cos\left\{\frac{\pi}{2} \frac{[(x-x_0)^2 + (y-y_0)^2]^{1/2}}{r_0}\right\}, \text{ wherein} \quad \text{[Equation 8]}$$

$(X_0, y_0)$ is a position of a center of the element plate, $\alpha_0$ is a value of $\alpha$ at the center, $r_0$ is a distance between the center and a point where $\alpha=0$, and, using the amplitude intensity $\alpha$ measured at each point within the aperture diameter, or when the photoelastic phase modulator is an element plate cut into a rectangle, the control/analysis unit determines two unknown parameters $y_0$ and $r_0$ by measuring amplitude intensity $\alpha$ at each point within the aperture, averaging values which are obtained at positions each having the same y and different x in a transverse direction, and performing fitting the averaged amplitude intensity $\alpha$ to a formula represented by the following equation:

$$\alpha = \alpha_0 \cos\left(\frac{\pi}{2} \frac{|y - y_0|}{r_0}\right), \text{ wherein} \quad \text{[Equation 9]}$$

$y_0$ is a height at the center in the minor axis direction, $\alpha_0$ is a value of $\alpha$ at the center, $r_0$ is a distance between the center and a point where $\alpha=0$, and, using the amplitude intensity $\alpha$ measured at each point within the aperture diameter, and thereby the control/analysis unit determines a calibration value for amplitude intensity $\alpha$ at each point within the aperture.

13. A polarization modulation imaging ellipsometer according to claim 1 or 2; wherein when the light source unit sequentially produces two kinds of measuring beams each having an ON duration of ¼ cycle and having a time lag of ¼ or ¾ cycle relative to an operation clock of the photoelastic phase modulator;

the control/analysis unit acquires output signals of the two-dimensional detector obtained by the sequential production of the two kinds of measuring beams, each measuring beam having a time lag of ¼ or ¾ cycle; calculates the $S_S$ value using the equation $S_S = S_4 - S_5$, wherein $S_4$ and $S_5$ denote the acquired output signals corresponding to time lags of ¼ or ¾ cycle; and denotes the $S_S$ value as $S_{S1}$;

when the light source unit sequentially produces two kinds of measuring beams each having an ON duration of ½ cycle and having a time lag of 0 or ½ cycle relative to an operation clock of the photoelastic phase modulator;

the control/analysis unit acquires output signals of the two-dimensional detector obtained by the sequential production of the two kinds of measuring beams, each measuring beam having a time lag of 0 or ½ cycle; calculates the $S_S$ value using the equation $S_S = S_6 - S_7$, wherein $S_6$ and $S_7$ denote the acquired output signals corresponding to time lags of 0 or ½ cycle; and denotes the $S_S$ value as $S_{S2}$; and the control/analysis unit calculates an actual measurement value of $S_{S1}/S_{S2}$, which is a ratio of two sine wave component values $S_{s1}$ and $S_{s2}$; and determines $J_S$, $J_C$, $J_0(\alpha)$ according to a look-up table obtained by calculation beforehand using a relationship expression represented by equation 10:

$$S_{S1}/S_{S2} = \frac{\sum_{m=0}^{\infty} \left\{(-1)^m \frac{J_{2m+1}(\alpha)}{2m+1} \sin[(2m+1)\pi/4]\right\}}{\sum_{m=0}^{\infty} \frac{J_{2m+1}(\alpha)}{2m+1}}. \quad \text{[Equation 10]}$$

14. A polarization modulation imaging ellipsometer according to claim 1 or 2; wherein the control/analysis unit acquires the output signals of the two-dimensional detector obtained by the sequential production of the measuring beams calculates the $S_S$; and the light source unit further sequentially produces two kinds of measuring beams represented by a formula $M_{3p}(t) = 1 + 2\cos[3\omega(t+p/6f) - \pi/2]$, wherein $\omega$ denotes an angular frequency of an operation clock of the photoelastic phase modulator, p is 0 or 1, and t is a time;

the control/analysis unit acquires output signals of the two-dimensional detector obtained by the sequential production of the two kinds of measuring beams calculates $S_{S3}$ by the equation $S_{S3} = S_{30} - S_{31}$ wherein $S_{30}$ and $S_{31}$ are the output signals corresponding to $M_{3p}$ with p=0 and 1, respectively; and the control/analysis unit calculates, setting $S_{S1}$ to $S_S$, an actual measurement value of $S_{S1}/S_{S3}$, which is a ratio of two sine wave component values $S_{S1}$ and $S_{S3}$; and determines $J_S$, $J_C$, and $J_0(\alpha)$ according to a look-up table obtained by calculation beforehand using a relationship expression represented by $S_{S1}/S_{S3}=J_1(\alpha)/J_3(\alpha)$.

15. A polarization modulation imaging ellipsometer according to claim 1 or 2, wherein
the light source unit further comprises a light source that sequentially emits light, and an amplitude modulator that modulates the light emitted from the light source at a predetermined frequency and outputs the modulated light as transmitted light.

16. A polarization modulation imaging ellipsometer according to claim 15, wherein
the amplitude modulator is a member selected from the group consisting of acousto-optical elements, electro-optical elements, and liquid crystal filters.

17. A polarization modulation imaging ellipsometer according to claim 15, wherein
the light source is a white light source;
the ellipsometer further comprises a monochromator or a narrow bandpass filter which splits the light emitted from the white light source, and inputs light of a predetermined wavelength into the amplitude modulator.

18. A polarization modulation imaging ellipsometer according to claims 1 or 2; wherein
the light source unit has a light emitting diode or diode laser, and a power supply capable of periodically changing output voltage; and
the power supply drives the light emitting diode or diode laser at a predetermined frequency.

19. A polarization modulation imaging ellipsometer according to claim 1 or 2; wherein
the two-dimensional detector is an imaging element using a CCD sensor or CMOS image sensor.

* * * * *